US006451976B1

(12) United States Patent
Lu et al.

(10) Patent No.: US 6,451,976 B1
(45) Date of Patent: Sep. 17, 2002

(54) BI-OR MULTIFUNCTIONAL MOLECULES BASED ON A DENDROASPIN SCAFFOLD

(75) Inventors: Xinjie Lu, London; Michael F. Scully, Crays Hill; Vijay V. Kakkar, Warsash; Kalwant S. Authi, Ilford, all of (GB)

(73) Assignee: Trigen Limited, London (GB)

( * ) Notice: Subject to any disclaimer, the term of this patent is extended or adjusted under 35 U.S.C. 154(b) by 0 days.

(21) Appl. No.: 09/381,546

(22) PCT Filed: Mar. 20, 1998

(86) PCT No.: PCT/GB98/00848

§ 371 (c)(1), (2), (4) Date: Sep. 20, 1999

(87) PCT Pub. No.: WO98/42834

PCT Pub. Date: Oct. 1, 1998

(30) Foreign Application Priority Data

Mar. 20, 1997 (GB) .............................................. 9705787

(51) Int. Cl.[7] .................................................. C07K 1/00

(52) U.S. Cl. ........................ 530/350; 530/350; 530/300; 435/6; 435/7.1; 536/23.1; 514/2

(58) Field of Search ................................ 530/350, 300; 536/23.1; 435/7.1, 6; 514/2

(56) References Cited

FOREIGN PATENT DOCUMENTS

| | | |
|---|---|---|
| WO | WO 92/07874 | 5/1992 |
| WO | WO 92/08804 | 5/1992 |
| WO | WO 94/14848 | 7/1994 |
| WO | WO 94/15953 | 7/1994 |
| WO | WO 98/42834 | * 10/1998 |

OTHER PUBLICATIONS

Lu et al., The Journal of Biological Chemistry, vol. 271, No. 1, pp. 289–294, 1/96.*

Joubert et al., Biochimica et Biophsica Acta, vol. 579, pp. 228–233, 1979.*

Alignment, Joubert et.al., Biochemica et Biophysica Acta vol. 579, pp. 228–233, 1979.*

Smith et al., "Protein Loop Grafting to Construct a Variant of Tissue–type Plasminogen Activator That Binds Platelet Integrin $\alpha_{IIb}\beta_3$," *Journal of Biological Chemistry,* 270(51):30486–30490 (Dec. 1996).

Lu et al., "Preferential antagonism of the interactions of integrin $\alpha_{IIb}\beta_3$ with immobilized glycoprotein ligands by snake–venom RGD (Arg–Gly–Asp) proteins," *Biochem J.,* 304:929–936 (1994).

Lu et al., "Synthetic RGD peptides derived from the adhesive domains of snake–venom–proteins: evaluation as inhibitors of platelet aggregation," *Biochem J.,* 296:21–24 (1994).

Lu, "Structure and Function Studies of The RGD–Protein Dendroaspin," Thesis submitted to the University of London, (Oct. 1995).

* cited by examiner

*Primary Examiner*—Karen Cochrane Carlson
*Assistant Examiner*—Hope A. Robinson
(74) *Attorney, Agent, or Firm*—Dorsey & Whitney LLP

(57) ABSTRACT

Dendroaspin, a polypeptide neurotoxin analogue is modified by recombinant DNA techniques, particularly "loop grafting" to provide a modified polypeptide. The modified polypeptide is constructed so as to retain dendroaspin activity, for example, platelet adhesion to fibrinogen, in addition to possessing one or more further biological or biochemical activities not native to dendroaspin, for example, platelet derived growth factor (PDGF) activity or hirudin activity.

40 Claims, 11 Drawing Sheets

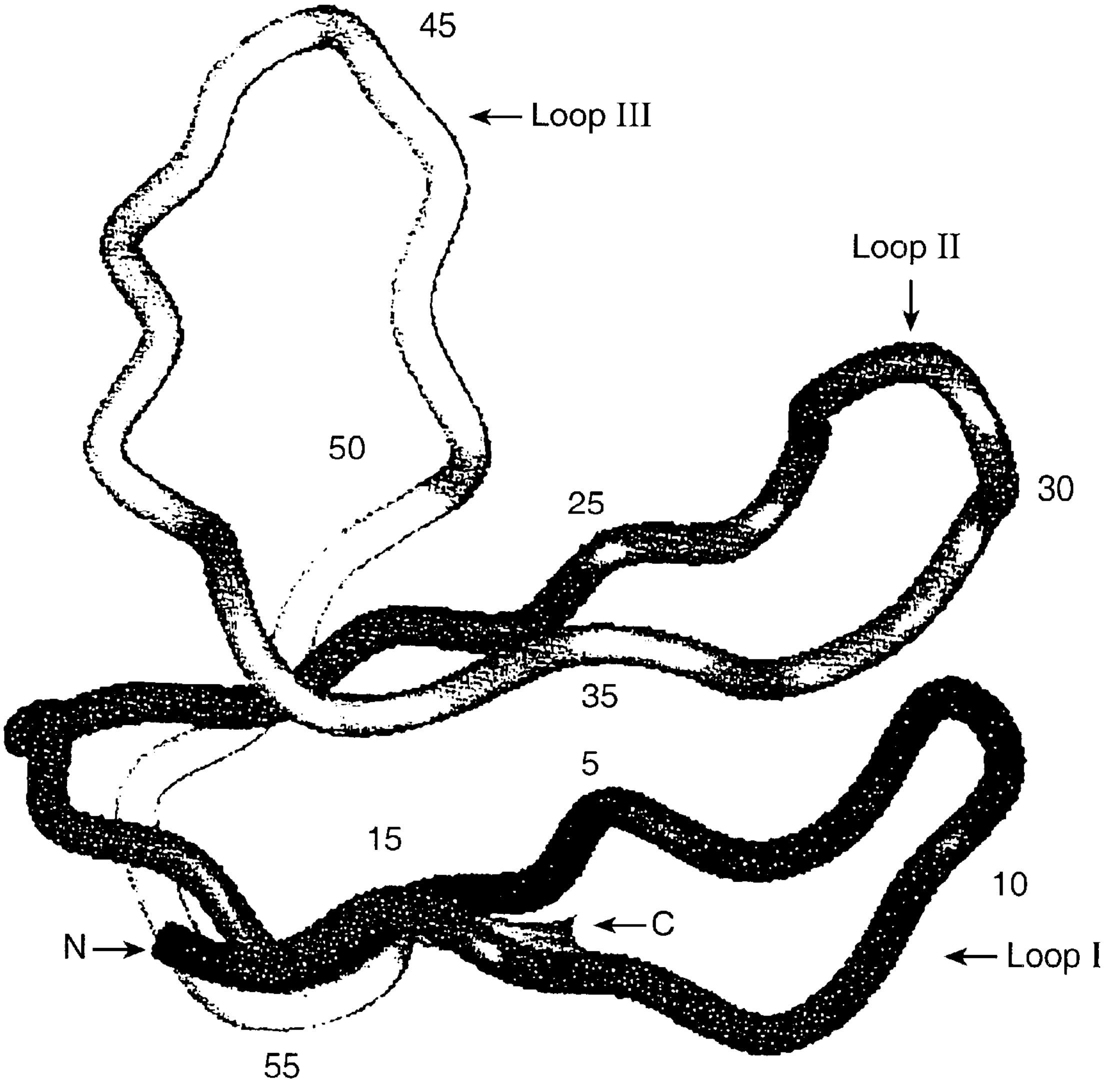
FIG._1

FXa

1

Glu.Gly.Ile.His.Ile.Glu.Gly.Arg.Arg-Ile-Cys-Tyr-Asn-His-Leu-Gly-Thr (1)

T GGG ATC CAT ATC GAA GGT CGT CGT ATC TGC TAC AAC CAT CTT GGT ACT

A CCC TAG GTA TAG CTT CCA GCA GCA TAG ACG ATG TTC GTA GAA CCA TGA (2)

Lys-Pro-Pro-Thr-Thr-Glu-Thr-Cys-Gln-Glu-Asp-Ser-Cys-Tyr-Lys-Asn (3)

AAA CCG CCG ACT ACT GAA ACT TGC CAG GAA GAC TCT TGC TAC AAA AAC

TTT GGC GGC TGA TGA CTT TGA ACG GTC CTT CTG AGA ACG ATG TTT TTG (4)

Ile-Trp-Thr-Phe-Asp-Asn-Ile-Ile-Arg-Arg-Gly-Cys-Gly-Cys-Phe-Thr (5)

ATC TGG ACT TTC GAC AAC ATC ATC CGT CGT GGT TGC GGT TGC TTC ACT

TAG ACC TGA AAG CTG TTG TAG TAG GCA GCA CCA ACG CCA ACG AAG TGA (6)

Pro-Arg-Gly-Asp-Met-Pro-Gly-Pro-Tyr-Cys-Cys-Glu-Ser-Asp-Lys-Cys (7)

CCG CGT GGT GAC ATG CCG GGT CCG TAC TGC TGC GAA TCT GAC AAA TGC

GGC GCA CCA CTG TAC GGC CCA GGC ATG ACG ACG CTT AGA CTG TTT ACG (8)

59

Asn-Leu *

(9)

AAC CTT TGA GAA TTC TCG TGA TGA

TTG GAA ACT CTT AAG AGC ACT ACT (10)

FIG._2A

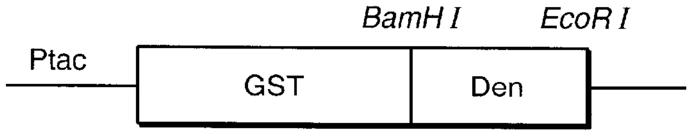

PGEX-DEG

FIG._2B

Sequence Alignment of Modified Dendroaspin

```
RICYNHLGTKPPTTET  CQEDSCYKNIWTFDNIIRRG   CGCFTPRGDMPGPYCCESDKCNL
---FTPR-DM-GPYPGP --------------------   -----------------------                        DEN-RGD1
----------------  ------ISRRLIDRTNANFL   -----------------------                        DEN-PDGF22
---FTPR-DM-GPYPGP ------ISRRLIDRTNANFL   -----------------------                        DEN-PDGF23
----------------  ------ISRRLIDRTNANFLPGP -----------------------                        DEN-PDGF24
---ISRRLIDRTNANFL --------------------   -----------------------                        DEN-PGDF1
---ISRRLIDRTNANFL ------RKIEIVRKK-----   -----------------------                        DEN-PDGF13
---GDTDLYDYYPEEDTE--------------------   -----------------------                        DEN-GP11
---GDGDFEEI-EEYL  -------------PRP----   -----------------------                        DEN-HR21
------------RP--  ------GDGDFEEIPEEYP-P  -----------------------                        DEN-HR22
----------------  ------PEGRILDDGF-TDIDE -----------------------                        DEN-TM2
----------------  ------GDTDLYDYYPEEDTE  -----------------------                        DEN-GP21
----------------  ------GDTDLYDYYPEEDTEPGP-----------------------                       DEN-GP22
---FTPR-DM-GPYPGP --------------------   ----------------FPRPQSHNDGDFEEIPEEYLQ        DEN-HR11
----------------  ------FTPRGDMPGPY      ----------------FPRPQSHNDGDFEEIPEEYLQ        DEN-HR21
----------------  --------------------   ----------------FPRPQSHNDGDFEEIPEEYLQ        DEN-HR22
---FTPR-DM-GPYPGP --------------------   ----------------PGPECPECYILDDGFICTDIDE       DEN-TM11
----------------  ------FTPRGDMPGPY      ----------------PGPECPECYILDDGFICTDIDE       DEN-TM21
----------------  --------------------   ----------------PGPECPECYILDDGFICTDIDE       DEN-TM22
```

FIG._3A

Alignment of the Amino Acid Sequences of Modified Dendroaspin

```
1   5   10   15   20   25   30   35   40   45   50   55          Activity
*   *    *    *    *    *    *    *    *    *    *    *
RICYNHLGTKPPTTETCQEDSCYKNIWTFDNIIRRGCGCFTPRGDMPGPYCCESDKCNL
---------------------------------------RI------DDR---------          -
---------------------------------------RRA---N-DDR---------          -
-----------------------------------------------DDR---------          -
---------------------------------------------N-------------          +
-----------------------------------------A---N-------------          +
----------------------------------------------A-A----------          -
----------------------------------------------A------------          +
------------------------------------------------A----------          +
----------------------------------------A------------------          Nd
---------------------------------------------F-------------
---------------------------------------------W-------------
---------------------------------------------S-------------
---------------------------------------------D-------------
---------------------------------------------H-------------
-------------------------------------------------R---------
-------------------------------------------------T---------
----------------------------------------------LD-----------
-----------------------------------------------DD----------
------------------------------------------K----------------
------------------------------------------K--W-------------
```

*..Denotes the antagonist activity using ADP-induced platelet aggregation; Nd, Not determined.

FIG._3B

```
Wild-type Den
    RICYNHLGTKPPTTET  CQEDSCYKNIWTFDNIIRRGCGCFTPRGDMPGPYCCESDKCNL
Den-Hr
    ---FTPRGDMPGPYPGP ----------------------------------FPRPQSHNDGDFEEIPEEYLQ
Den-Tm
    ---FTPRGDMPGPYPGP ----------------------------------ECPEGYILDDGFICTDIDE
Den-Gb
    ---FTPRGDMPGPYPGP ----------------------------------GDTDLYDYYPEEDTE
Den-Tb
    ---FTPRGDMPGPYPGP --------------------PGPTWTANVGKGQPS
Den-Pd
    ---FTPRGDMPGPYPGP ------ISRRLIDRTNANFL-----------------------
```

Abbreviations are: Den, Dendroaspin; Tm, Thrombomodulin; Hr, Hirudin; Pd, PDGF; Gb, Glycoprotein IB; Tb, Thrombin.

Figure 1 Sequence Alignment of Dendroaspin and Modified Dendroaspins

```
Wild-type Den    RICYNHLGTKPPTTET CQEDSCYKNIWTFDNIIRRGCGCFTPRGDMPGPYCCESDKCNL
Den-Hr           ---FTPR-DM-GPYPGP----------------------------------FPRPQSH-DGDFEEIPEEYLQ
Den-Tm           ---FTPR-DM-GPYPGP----------------------------------E-PEGYILDDGFICTDIDE
Den-Gb           ---FTPR-DM-GPYPGP----------------------------------GDTDLYDYYPEEDTE
Den-Tb           ---FTPR-DM-GPYPGP--------------------P-PTWTANVGK-QPS
Den-Pd           ---FTPR-DM-GPYPGP------ISRRLIDRTNANFL-----------------------
```

Abbreviations are: Den, Dendroaspin; Tm, Thrombomodulin; Hr, Hirudin; Pd, PDGF; Gb, Glycoprotein IB; Tb, Thrombin.

FIG._3C

| Engineered Molecules | Foreign Proteins from which the Sequences Derived | PDGF Antagonist | Prolong Thrombin Clotting Time | Inhibiting Platelet Aggregation Induced by | |
|---|---|---|---|---|---|
| | | | | ADP | Thrombin |
| Wild-type | | | | | |
| Den | | | | + | |
| Den-Hr | Hirudin | | + | + | + |
| Den-Tm | Thrombomodulin | | + | + | + |
| Den-Gb | Glycoprotein IB | | + | + | + |
| Den-Tb | Thrombin | | + | + | + |
| Den-Pd | PDGF | + | | + | |

FIG._3D

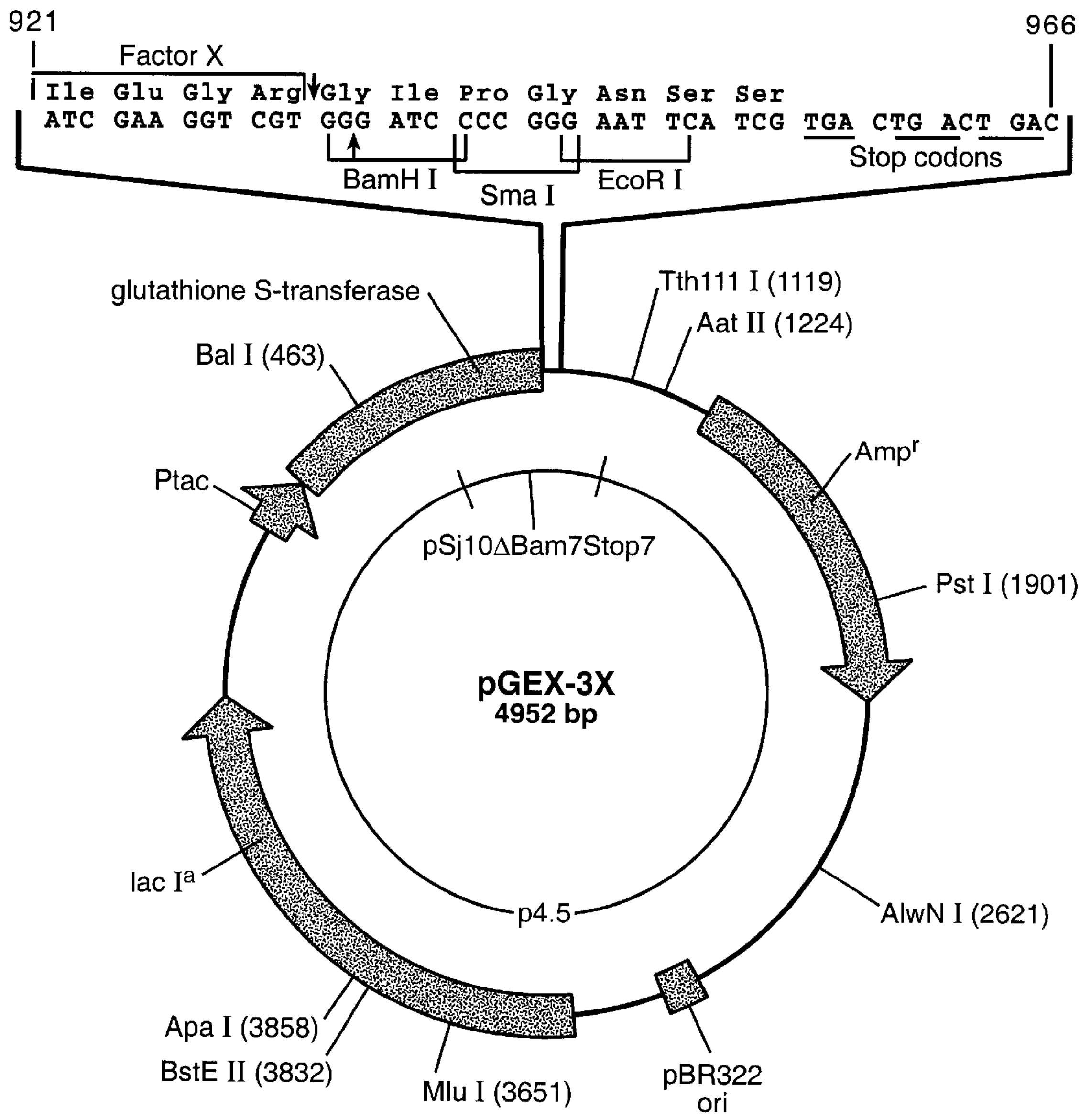
*FIG._4*

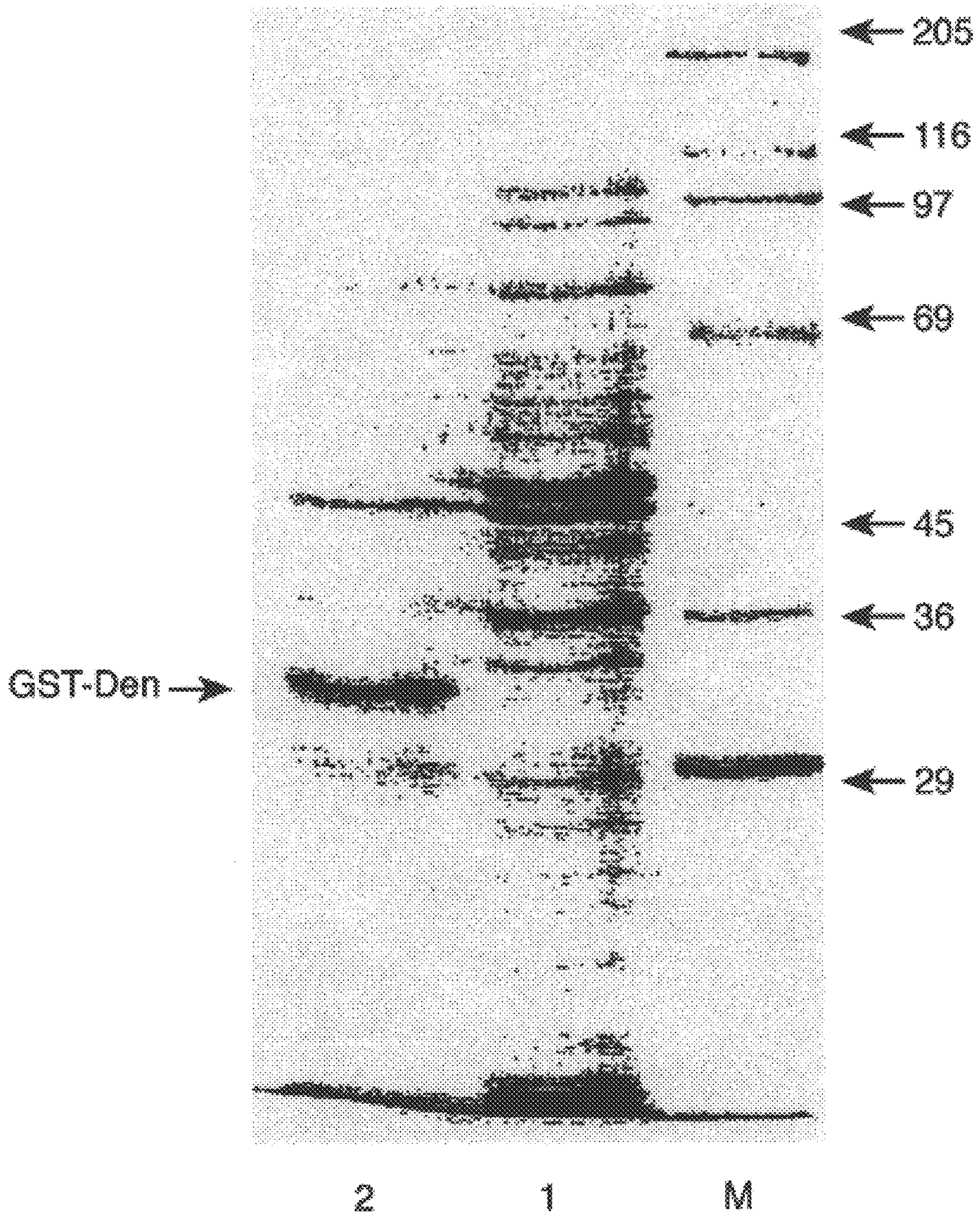
FIG._5A

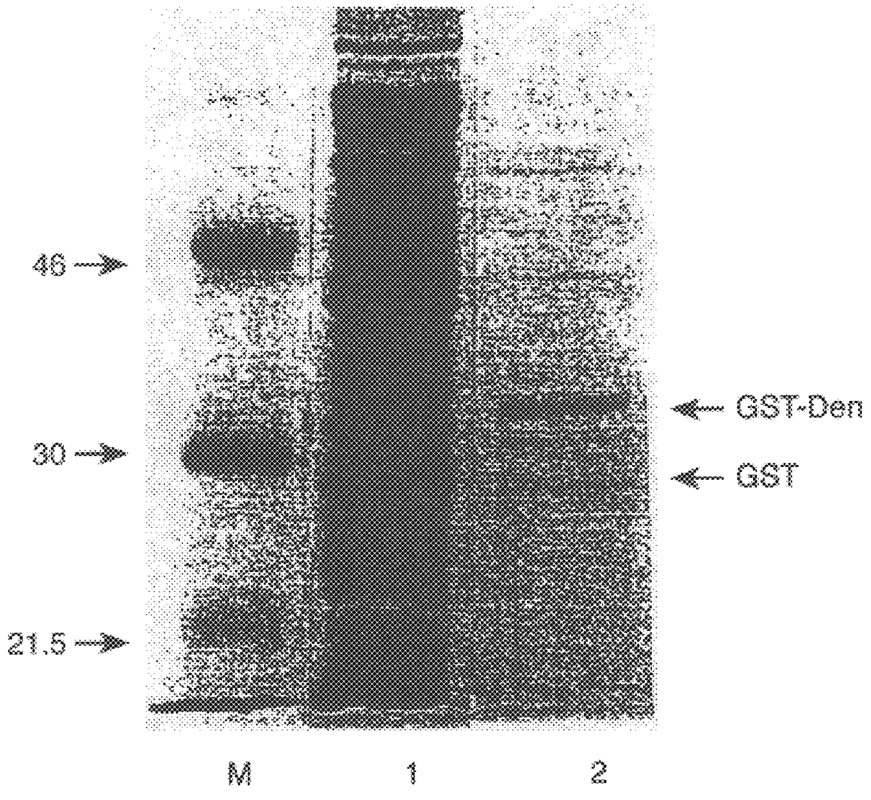
FIG._5B
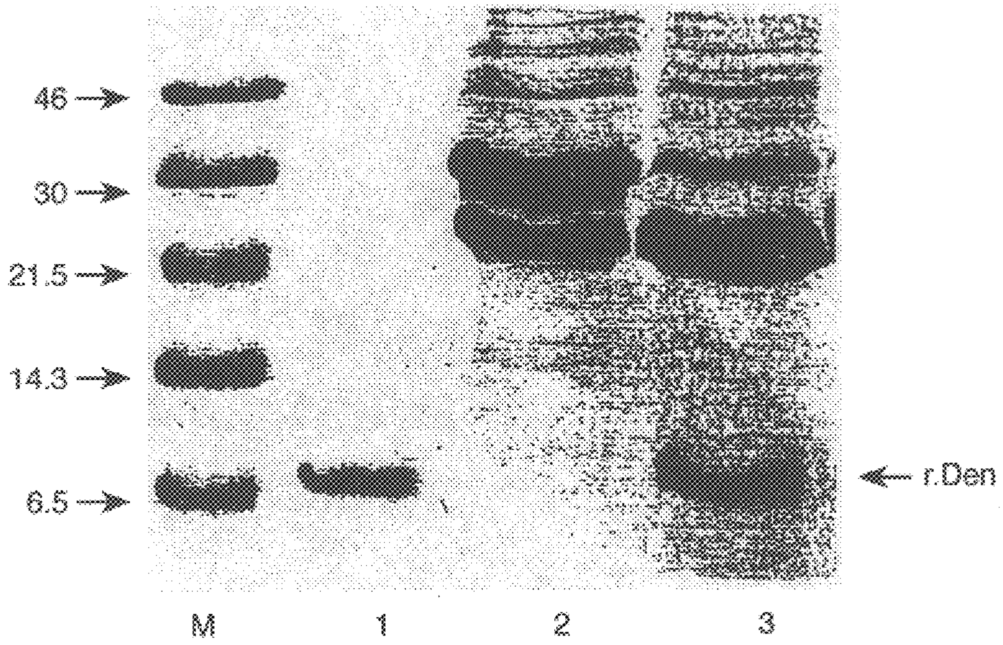
FIG._5C

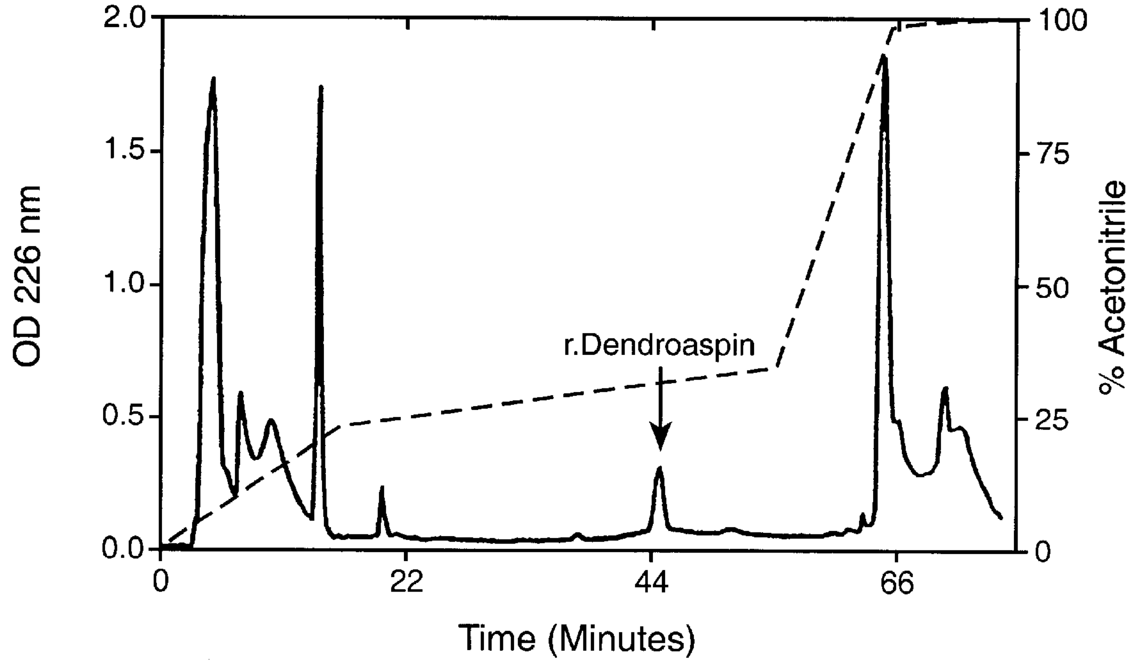
*FIG._6A*
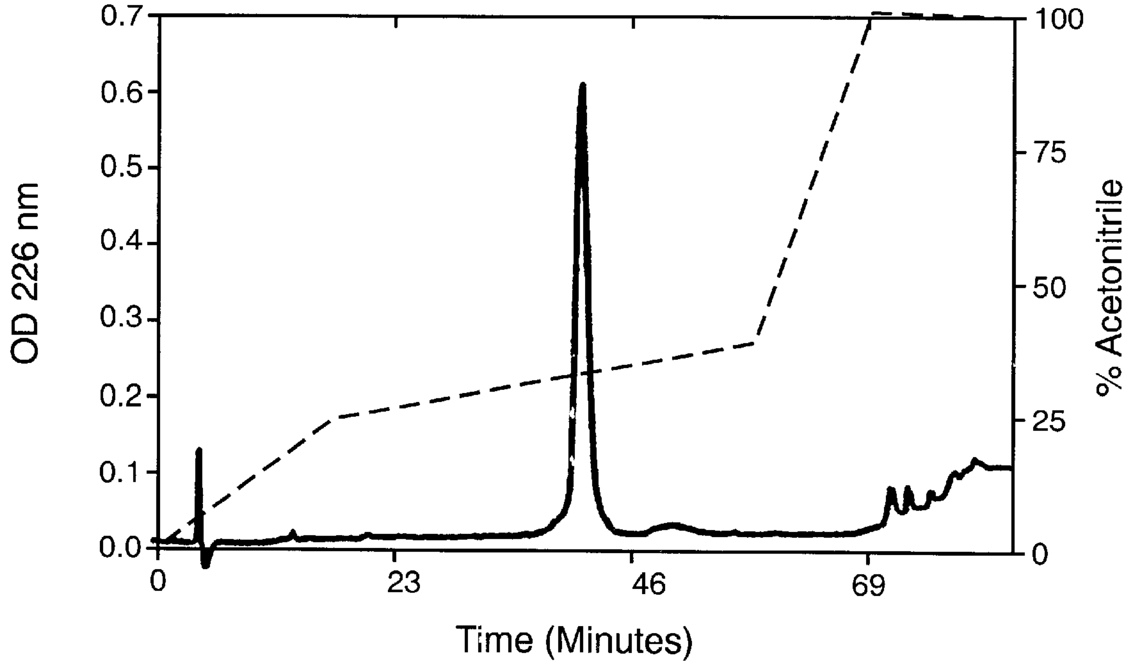
*FIG._6B*

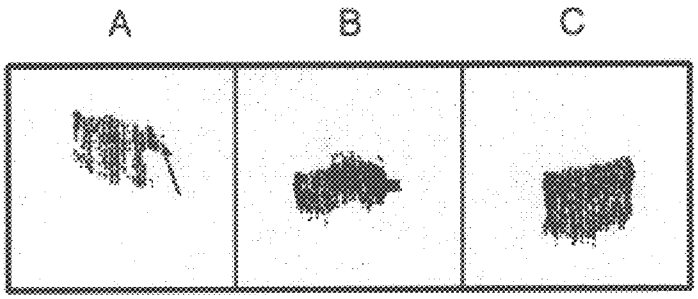
A: R38; B: R65 and C: R51
FIG._7
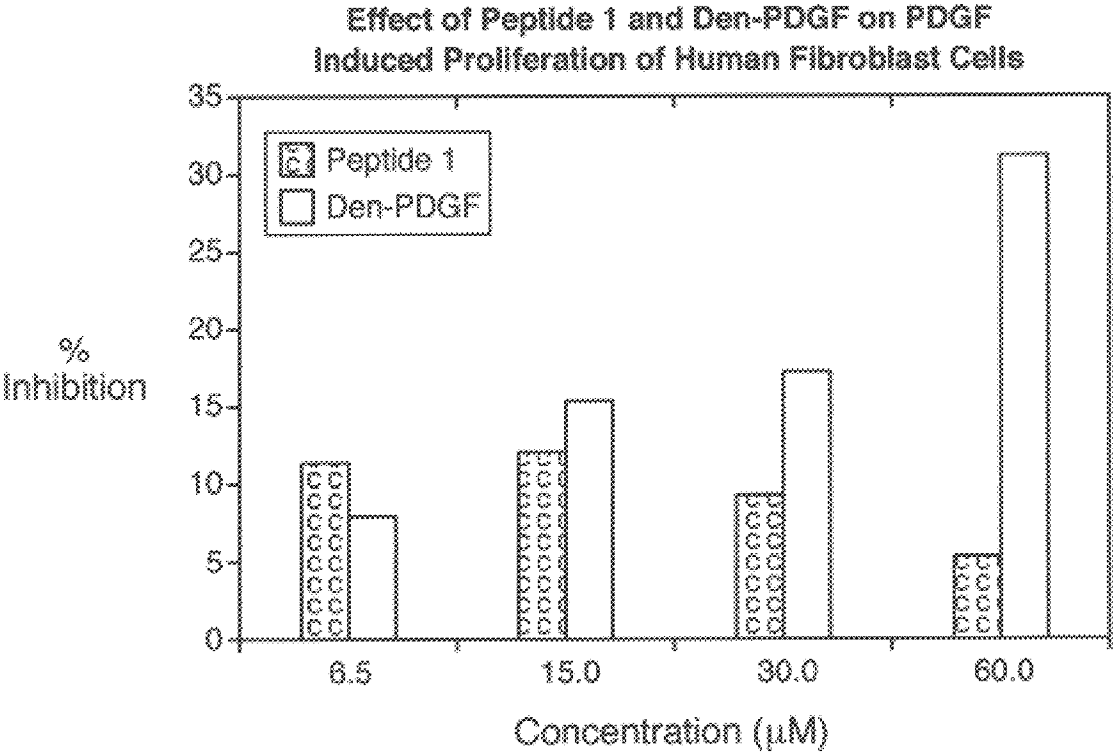
FIG._8

BI-OR MULTIFUNCTIONAL MOLECULES BASED ON A DENDROASPIN SCAFFOLD

This application is a national stage application of PCT/GB 98/00848, filed Mar. 20, 1998, which claims foreign priority to GB 97 05787.1 filed Mar. 20, 1997.

The present invention relates to dendroaspin-based chimeric molecules which have anticoagulant, antiplatelet and other activities. The invention also relates to nucleic acid molecules encoding these chimeric dendroaspin molecules, cloning and expression vectors comprising such nucleic acids and host cells transformed with expression vectors so as to provide recombinant chimeric multifunctional dendroaspin. The invention further relates to pharmaceutical compositions comprising chimeric dendroaspin for use in the prevention or treatment of disease associated with thrombus formation or platelet aggregation. The invention also further relates to the use of a dendroaspin scaffold in the design and generation of chimeric dendroaspin derivatives having inhibitory activity against integrin binding activity of platelets plus some further functionality such as an anticoagulant or antithrombotic action.

The role of blood coagulation is to provide an insoluble fibrin matrix for consolidation and stabilization of a haemostatic plug. Formation of a cross-linked fibrin clot results from a series of biochemical interactions involving a range of plasma proteins.

Acute vascular diseases, such as myocardial infarction, stroke, pulmonary embolism, deep vein thrombosis and peripheral arterial occlusion are caused by either partial or total occlusion of a blood vessel by a blood clot.

The formation of a blood clot within a blood vessel is termed thrombosis and is dependent upon platelet aggregation. In the context of blood vessel injury (such as that which might arise in surgical procedures) the interaction of blood platelets with the endothelial surface of injured blood vessels and with other platelets is a major factor in the course of development of clots or thrombi.

Various agents for preventing formation of blood clots are now available, such as aspirin, dipyridamole and filopidine. These products generally inhibit platelet activation and aggregation, or delay the process of blood coagulation but they have the potential side effect of causing prolonged bleeding. Moreover, the effect of such products can only be reversed by new platelets being formed or provided.

Platelet aggregation is dependent upon the binding of fibrinogen and other serum proteins to the glycoprotein receptor IIb/IIIa complex on the platelet plasma membrane. GP IIb/IIIa is a member of a large family of cell adhesion receptors known as integrins, many of which are known to recognize an Arg-Gly-Asp (RGD) tripeptide recognition sequence.

Heparin and low molecular weight heparins have been used widely to treat conditions, such as venous thromboembolism, in which thrombin activity is responsible for the development or expansion of a thrombus. Although effective, heparin produces many undesirable side effects, including haemorrhaging and thrombocytopenia. A more specific and less toxic anticoagulant is therefore required.

Direct thrombin inhibitors are available and examples of these are hirudin, hirugen and hirulog (the latter two being synthetic hirudin derivatives), PPACK (a synthetic tripeptide) and argatroban (an arginine derivative). The actions of these inhibitors are reviewed in Lefkovits J and Topol E J (1994), Circulation 90:1522–1536. Although in theory, the bleeding risk with direct thrombin inhibitors is lower than with other antithrombotics because of their mono-target specificity, absence of direct platelet effects, and short half-life, bleeding still remains as the most concerning adverse effect.

There are a range of other thrombin inhibitors which have been developed (listed in table 1 of Lefkovits J and Topol E J supra) but these have turned out to be just too toxic for clinical use.

Localized narrowing of an artery caused by atherosclerosis is a condition which can usually be remedied surgically by the technique of balloon angioplasty. The procedure is invasive and causes some tissue damage to the arterial wall which can result in thrombus formation. Extracellular proteins such as fibronectin in the arterial wall become exposed to blood in the artery. Platelets bind to the RGD motif of fibronectin via integrin receptors which in turn leads to platelet aggregation and the start of the cascade of clotting reactions. An agent which specifically inhibits platelet aggregation at the sites of damage and which also inhibits clotting at these sites is required. The agent should be non-toxic and free of undesirable side effects such as a risk of generalized bleeding.

Integrins are a family of cell surface receptors that mediate adhesion of cells to each other or to the extracellular matrix (Kieffer N & Philips D R (1990) Annu Rev Cell Biol 6: 329–357; Hynes R O (1992) Cell 69: 11–25; McEver R P (1992) Curr Opin Cell Biol 4: 840–849; Smyth S S et al (1993) Blood 81: 2827–2843; Giancotti F G and Mainiero F (1994) Biochim Biophys Acta 1198: 47–64). They are composed of noncovalently associated $\alpha$ and $\beta$ transmembrane subunits. There exist 16 different $\alpha$ and $\beta$ different $\beta$ subunits that heterodimerize to produce about 20 different kinds of receptors (Clark E A & Brugge J S (1995) Science 268: 233–239). Among the integrins, the platelet membrane integrin $\alpha_{IIb}\beta_3$ is one of the best characterized. Upon cell activation, the $\alpha_{IIb}\beta_3$ integrin binds several glycoproteins, predominantly through the Arg-Gly-Asp (RGD) tripeptide sequence (Pierschbacher M D and Ruoslahti E (1984) supra; Plow E F et al (1987) Blood 70: 110–115; Pytela R et al (1986) Science 231: 1559–1562) present in fibrinogen (Nachman R L and Nachman L L K (1992) J Clin Invest 69: 263–269), fibronectin (Gardner J M and Hynes R O (1985) Cell 42: 439–448), von Willebrand factor (Ruggeri Z et al (1983) J Clin Invest 72: 1–12), vitronectin (Pytela R M et al (1985) Proc Natl Acad Sci USA 82: 5766–5770), and thrombospondin (Karczewski J et al (1989) J Biol Chem 264: 21322–21326). The nature of the interactions between these glycoprotein ligands and their integrin receptors is known to be complex, and conformational changes occur in both the receptor (Sims P J et al (1991) J Biol Chem 266: 7345–7352) and the ligand (Ugarova T et al (1995) Thromb Haemostasis 74: 253–257).

Recently, many proteins from a variety of snake venoms have been identified as potent inhibitors of platelet aggregation and integrin-dependent cell adhesion. The majority of these proteins which belong to the so-called "disintegrin" family share a high level of sequence homology, are small (4–8 kDa), cysteine-rich and contain the sequence RGD (Gould R J et al (1990) Proc Soc Exp Biol Med 195: 168–171) or KGD (Scarborough R M et al (1991) J Biol Chem 266: 9359–9362). In addition to the disintegrin family, a number of non-disintegrin RGD proteins of similar inhibitory potency, high degree of disulfide bonding, and small size have been isolated from both the venoms of the Elapidae family of snakes (McDowell R S et al (1992) Biochemistry 31: 4766–4772; Williams J A et al (1992) Biochem Soc Trans 21: 73S) and from leech homogenates (Knapp A et al (1992) J Biol Chem 267: 24230–24234). All of these proteins are approximately 1000 times more potent inhibitors of the interactions of glycoprotein ligands with the integrin receptors than simple linear RGD peptides; a feature that is attributed to an optimally favourable conformation of the RGD motif held within the protein scaffold. The NMR structures of several inhibitors including kistrin (Adler M et al (1991) Science 253: 445–448; Adler M and Wagner G (1992) Biochemistry 31: 1031–1039; Adler M et al (1993) Biochemistry 32: 282–289), flavoridin (Senn H and Klaus W (1993) J Mol Biol 234: 907–925), echistatin (Saudek V et al (1991) Biochemistry 30: 7369–7372; Saudek V et al (1991) Eur J Biochem 202: 329–328; Cooke R M et al (1991) Eur J Biochem 202: 323–328; Cooke R M et al (1992) Protein Eng 5: 473–477), albolabrin (Jaseja M et al (1993) Eur J Biochem 218: 853–860), decorsin (Krezel A M et al (1994) Science 264: 1944–1947), and dendroaspin (Jaseja M et al (1994) Eur J Biochem 226: 861–868; Sutcliffe M J et al (1994) Nature Struct Biol 1: 802–807) have been reported, and the only common structural feature elucidated so far is the positioning of the RGD motif at the end of a solvent exposed loop, a characteristic of prime importance to their inhibitory action.

Recent studies have implied a role for the amino acids around the tripeptide RGD in regulating the ligand binding specificity shown by snake venom proteins. Scarborough R M et al (1993) J Biol Chem 268: 1058–1065 examined a range of disintegrins and observed that those containing RGDW were very effective at inhibiting the interactions of fibrinogen to purified $\alpha_{IIb}\beta_3$ but not of vitronectin and fibronectin to purified $\alpha_v\beta_3$ and $\alpha_5\beta_1$, respectively, whereas the converse was true for disintegrins containing the sequence RGDNP. Other regions of amino acid sequence divergence may also be contributory (Scarborough et al (1993) supra).

Dendroaspin, a short chain neurotoxin analogue containing the RGD sequence, and the disintegrin kistrin, which show little overall sequence homology but have similar amino acids flanking the RGD sequence (PRGDMP), are both potent inhibitors of platelet adhesion to fibrinogen but poor antagonists of the binding of platelets to immobilized fibronectin (Lu X et al (1994) Biochem J 304: 929–936). In contrast, elegantin, which has 65% sequence homology to kistrin but markedly different amino acids around RGD (ARGDNP), preferentially inhibited platelet adhesion to fibronectin as opposed to fibrinogen and binds to an allosterically distinct site on the $\alpha_{IIb}\beta_3$ complex.

Smith J W et al (1995) Journal of Biological chemistry 270: 30486–30490 undertook protein “loop grafting” experiments to construct a variant of tissue-type plasminogen activator (t-PA) which bound platelet integrin $\alpha_{IIb}\beta_3$. Amino acids in a surface loop of the epidermal growth factor (EGF) domain of t-PA were replaced with residues from a complementarity-determining region (CDR) forming one CDR of a monoclonal antibody reactive against the adhesive integrin receptor $\alpha_{IIb}\beta_3$. The resulting variant of t-PA (loop-grafted-t-PA) bound $\alpha_{IIb}\beta_3$ with nanomolar affinity and had full activity to both synthetic and natural substrates. The effects and applicability of loop grafting are altogether unpredictable and uncertain.

The present inventors have now discovered that the dendroaspin scaffold lends itself to modification. When dendroaspin (including the RGD motif) is modified to incorporate further functional amino acid sequences for example active portions or motifs of agonists, antagonists or inhibitors of factors in the clotting cascade, the resulting molecules are particularly useful as anticoagulants and do not suffer from the drawbacks associated with existing anticoagulants.

In first aspect the present invention provides a hybrid polypeptide comprising a first amino acid sequence including the RGD motif and conferring dendroaspin activity and a further amino acid sequence conferring activity other than that of dendroaspin activity.

The invention also provides a hybrid polypeptide having integrin binding activity comprising a dendroaspin scaffold and a further non-dendroaspin amino acid sequence, preferably of different activity.

Advantageously, the molecules of the invention have an integrin binding activity which when administered in vivo results in the binding of the molecules to platelets thereby inhibiting the aggregation of the platelets, at sites of injury. Moreover, the non-wild-type dendroaspin domain provides secondary, optionally further functionality eg antithrombotic action, inhibiting cell migration and proliferation and regulating signal transduction. Molecules of the invention are therefore bi- or multifunctional in their activities against blood coagulation, particularly thrombus formation and arterial/venous wall thickening at the sites of injury. Polypeptides of the invention may have activities against leukocyte recruitment, immune system activation, tissue fibrosis and tumorigenesis.

The polypeptide of the invention may comprise at least two said further amino acid sequences, preferably the two said further sequences are the same.

The further amino acid sequence may comprise two or more amino acid sequence portions separated by at least one amino acid residue of dendroaspin. The two or more sequence portions may be transposed with respect to one another and to the linear order of amino acids in the native further amino acid sequence. In other words, the native order of the two or more amino acid sequence portions is altered although the actual sequence of each portion may not necessarily be altered.

The said further sequence may be selected from platelet derived growth factor (PDGF), glycoprotein (GP) IBα, hirudin, thrombin, throinbomodulin (particularly the fifth EGF-like domain thereof), vascular epidermal growth factor (VEGF), transforming growth factor-β1 (TGFβ1), basic fibroblast growth factor (bFGF), angiotensin II (Ang II), factor VIII and von willebrand factor (vWF).

In this way the molecules of the invention may be rendered multifunctional so that they are active against more than just platelet aggregation, for example another component in the clotting cascade (eg thrombin activity), or the intracellular signaling cascade (eg growth factor). The modified dendroaspins of the invention may he engineered so that the further amino acid sequence has integrin binding activity, hereby providing a dendroaspin based molecule with augmented integrin binding activity.

The polypeptide of the invention preferably comprises an amino acid sequence as shown in FIG. 3 (SEQ ID NO:4). Prior to inclusion of said further amino acid sequence the dendroaspin scaffold of the invention includes homologous molecules which may share about 50% amino acid sequence homology, preferably about 65%, more preferably about 75% and even more preferably about 85% homology with dendroaspin.

Excluding the nucleic acid sequence encoding said further amino acid sequence nucleic acid sequences encoding the polypeptide of the invention may share about 50% nucleotide sequence homology, preferably about 65%, more preferably about 75% and even more preferably about 85% homology with a dendroaspin nucleotide sequence.

The polypeptides of the invention may comprise a greater or lesser number of amino acid residues compared to the 59 amino acids of dendroaspin. For example, the molecules of the invention may comprise a number of amino acid residues in the range 45 to 159, preferably about 49 to 85, more preferably about 53 to 69, even more preferably about 57 to 61.

The further amino acid sequence is preferably incorporated into (a) loop I and/or loop II; (b) loop I and/or loop III; (c) loop II and/or loop III; or (d) loop I, loop I and loop III of the dendrcaspin scaffold. Loop I comprises amino acid residues 4–16, loop II residues. 23–36 and loop III residues 40–50. However, the further amino acids being incorporated may extend into or substitute regions external to the loops, ie residues 1–3, 17–22 and 37–39 such that residues of the non-loop regions are augmented or substituted for those of the further amino acid sequence or sequences being inserted.

The further amino acid residues are preferably incorporated into either loop I or loop II. In this way the RGD-containing loop III is unaltered and so the integrin binding function of dendroaspin is retained.

A further RGD motif may be introduced into the dendroaspin scaffold, preferably into loop I or loop II, thereby increasing dendroaspin activity.

A preferred location for the inserted further sequence is at a site in dendroaspin scaffold between amino acid residues: 4–16, 18–21, 23–36, or 52–59.

Each inserted further amino acid sequence or portion of a further amino acid sequence is preferably an amino acid sequence in the range 3–40 amino acid residues, more preferably 3–16, even more preferably 3–14 amino acid residues long. The start of the inserted further amino acid sequence may be at any one of amino acid residues 1–57 of the dendroaspin scaffold. The end of the inserted further amino acid sequence may be at any one of amino acid residues 3–59 of the dendroaspin scaffold.

When two further amino acid sequences are inserted into the dendroaspin scaffold then the linear distance between these is preferably in the range 1–35 amino acids, more preferably 1–14 amino acids. When more than two further amino acid sequences are inserted then there is preferably at least one native dendroaspin amino acid residue separating each further amino acid sequence.

The RGD-containing loop may be modified by insertion, deletion or substitution of one of more amino acid residues, preferably a maximum of 8 or a minimum of 1 amino acids can be modified within loop III of dendroaspin.

The RGD loop preferably has an amino acid sequence as shown in FIG. 3B (residues 40–50 of SEQ ID NO:4). An advantage of modifying the RGD loop region is that the integrin binding activity may be enhanced and become more specific for certain glycoprotein ligands. Also, if one or more of the "foreign" further amino acid sequences grafted into the dendroaspin scaffold has steric effects on the RGD motif then loop III around the RGD site can be modified to overcome any steric hindrance thereby restoring, perhaps enhancing RGD functionality.

Loop I and/or loop II may be modified by insertion, deletion or substitution of one or more amino acid residues. Any suitable number of amino acids can be inserted into the dendroaspin scaffold to give the desired bi- or multi-functional activity although a number of residues in the range 14 to 36 are preferred for insertion at one or more sites in the dendrcaspin scaffold.

Modification of the loops may become necessary if a "foreign" further amino acid sequence grafted into the dendroaspin scaffold has a steric hindrance effect either on another grafted domain or on the RGD-containing loop. Computer assisted molecular modelling using Insight II software (Molecular Simulations Inc) can be used to predict the structure of the "loop grafted" dendroaspins of this invention. In instances where steric effects between the loops may serve to cause loss of functionality, these effects can be "designed out" by modifying appropriate parts of the dendroaspin molecule in an appropriate way. Sometimes this may involve inserting a number of suitable amino acid residues to extend one or more of the loop structures.

Preferred modification includes the insertion of polyglycine into the loop or loops of the dendroaspin scaffold in order to extend them. Other modifications comprising repeat units of an amino acid residue or number of residues can be used. Computer modelling studies can be used to design the loop modifications needed in order to extend the loops of dendroaspin.

In the design of a bifunctional or multifunctional molecule in accordance with the invention, "fine tuning" of activity, stability or other desired biological or biochemical characteristic may be achieved by altering individual selected amino acid residues by way of substitution or deletion. Modification by an insertion of an amino acid residue or residues at a selected location is also within the scope of this "fine tuning" aspect of the invention. The site-directed mutagenesis techniques available for altering amino acid sequence at a particular site in the molecule will be well known to a person skilled in the art.

In second aspect the invention provides a nucleic acid molecule encoding a polypeptide as hereinbefore defined.

The nucleic acid may be linked operatively to a promoter and optionally to a nucleic acid sequence encoding a heterologous protein or peptide thereby to encode a fusion product. The promoter is preferably β-D-isopropyl-thiogalactopyranoside (IPTG) inducible and the heterologous protein or peptide may be glutathione S-transferase (GST).

This aspect of the invention also includes a plasmid comprising a nucleic acid as hereinbefore defined. The plasmid is preferably pGEX-3X.

In third aspect the invention provides a host cell transformed with a plasmid as hereinbefore defined, preferably said host cell is *E coli.*

The invention therefore also provides a cell culture comprising transformed host cells as hereinbefore defined.

In fourth aspect the invention provides a method of producing a polypeptide as hereinbefore defined comprising culturing a host cell as hereinbefore defined so as to express said polypeptide, extracting the polypeptide from the culture and purifying the same.

In fifth aspect, the invention provides a method of producing a multifunctional anticoagulant comprising the steps of:

a) constructing an expression vector comprising a nucleic acid sequence encoding a dendroaspin scaffold operatively linked to a promoter and optionally linked to nucleic acid encoding an heterologous protein for co-expression therewith.

b) modifying at least a portion of the nucleic acid sequence of the vector encoding the dendroaspin scaffold, excluding the RGD motif, by one or more of insertion, deletion or substitution of nucleic acid residues so that on expression the dendroaspin scaffold comprises a further amino acid sequence of activity other than that of dendroaspin activity.

c) transforming a host cell with the vector and causing the host cell to express the modified dendroaspin nucleic acid sequence.

The method preferably further comprises the steps of:

d) extracting the modified dendroaspin from a host cell culture, e) purifying the modified dendroaspin from the cell culture extract, optionally including the step of cleaving the dendroaspin from a co-expressed heterologous protein.

The heterologous protein is preferably GST and the purification preferably involves affinity chromatography using glutathione Sepharose 4B contained in the GST purification modules followed by factor Xa-mediated cleavage of the modified dendroaspins from GST.

The invention therefore provides a polypeptide as hereinbefore defined obtainable by the method of producing a multifunctional anticoagulant as defined above.

In sixth aspect the invention provides a pharmaceutical composition comprising a therapeutically effective amount of a polypeptide as hereinbefore defined, optionally further comprising a pharmaceutically acceptable excipient or carrier. A multiplicity of polypeptides of the invention of different functionalities may be combined together in a pharmaceutically acceptable form so as to provide a desired treatment. A multiplicity of polypeptides of the invention of different functionalities may be combined together in a pharmaceutically acceptable form so as to provide a desired treatment.

The polypeptide of the invention is preferably formulated for intravenous injection or intravenous infusion although other methods of administration are possible, eg subcutaneous or intramuscular should it be desired to provide a slow release into the circulatory system of an individual. Also possible is the formulation of the polypeptide for use with implanted controlled release devices such as those used to administer growth hormone for example.

One formulation may comprise extravasated blood combined with a polypeptide of the invention at a concentration in the range 1 nM–60 $\mu$M. This blood may be stored in ready to use form and provides an immediate and convenient supply of blood for transfusion in cases when clotting must be avoided such as during or immediately following surgical procedures.

In seventh aspect the invention provides a polypeptide as hereinbefore defined for use as a pharmaceutical.

In eighth aspect the invention provides for the use of a polypeptide as hereinbefore defined for the manufacture of a medicament for the treatment of disease associated with thrombosis; more particularly thrombosis, myocardial infarction, retinal neovascularization, endothelial injury, dysregulated apoptosis, abnormal cell migration, leukocyte recruitment, immune system activation, tissue fibrosis and tumorigenesis.

The invention also provides methods for the treatment of disease associated with thrombosis; more particularly thrombosis, myocardial infarction, retinal neovascularization, endothelial injury, dysregulated apoptosis, abnormal cell migration, leukocyte recruitment, immune system activation, tissue fibrosis and tumorigenesis. The methods comprise administering a therapeutically effective amount of a polypeptide as hereinbefore defined.

Preferred embodiments of the invention will now be described and with reference to the following examples and drawings in which:

FIG. 1 shows the basic three-dimensional structure of a molecule of dendroaspin. N denotes the —NH terminus and —C denotes the —COOH terminus. Amino acid residues are numbered.

FIG. 2A shows the nucleotide (SEQ ID NO:2) and corresponding amino acid sequences (SEQ ID NO:1) of dendroaspin. Individual synthetic oligonucleotides are indicated by numbers 1–10.

FIG. 2B is a partial restriction map of plasmid pGEX-DEG.

FIG. 3A (SEQ ID NOS:4–22) comprises alignments of modified dendroaspins where the inserted amino acid sequences are listed beneath the amino acid sequence of dendroaspin.

FIG. 3B (SEQ ID NOS:4, 23–42) is like FIG. 3A and further alignments of the amino acid sequences (one letter code) of various modified dendroaspins.

FIG. 3C (SEQ ID NOS:4, 43–46, 7) is like FIG. 3A and shows modified molecules of the invention.

FIG. 3D is a table showing various activities of the modified molecules of the invention.

FIG. 4 shows the expression plasmid pGEX-3X (SEQ ID NOS:47–48) used to clone and express modified dendroaspin fusion protein.

FIG. 5A shows a 12.5% SDS-PAGE gel comparing the total cellular lysates of either induced (lane 1) or uninduced (lane 2) bacteria transformed with the recombinant plasmid pGEX-DEG harbouring the modified dendroaspin gene.

FIG. 5B shows a 10% SDS-PAGE gel comparing total cell lysate (lane 1) from induced bacteria transformed with pGEX-DEG and an affinity purified extract of such a lysate (lane 2).

FIG. 5C shows a 20% SDS-PAGE gel of affinity purified and factor Xa digested GST-modified dendroaspin fusion protein. Lane 1 is dendroaspin, lane 2 is GST-Den and lane 3 is factor Xa digested GST-Den FIG. 6A is a reverse phase HPLC elution profile of recombinant dendroaspin purified on a Vydac $C_{18}$ column developed with an acetonitrile gradient (the retention time of recombinant dendroaspin at 44 minutes was indicated by an arrow).

FIG. 6B is a reverse phase HPLC elution profile of the peak fraction eluting at 44 minutes in FIG. 6A carried out under similar conditions.

FIG. 7 shows immunoprecipitation of dendroaspin containing PDGF loop I using antibodies R38 and R65 raised to loop I and R51 raised to both loop I and loop III. A 32 kDa protein which corresponds to the GST-mutant dendroaspin was observed. Lane 1 is DEN-PDGF probed with R38, lane 2 probed with R65 and lane 3 probed with R51.

FIG. 8 is a bar chart showing the results of an experiment in which PDGF-dendroaspin is used to inhibit PDGF induced proliferation of human fibroblast cells. "Peptide 1" corresponds to the linear amino acid sequence of PDGF loop I.

Dendroaspin is a short chain neurotoxin homologue from the venom of Elapidae snakes, which lacks neurotoxicity. Unlike neurotoxins, it contains an Arg-Gly-Asp-(RGD)-motif and functions as an inhibitor of platelet aggregation and platelet adhesion with comparable potency to the disintegrins from the venoms of Viperidae. The structure of dendroaspin in solution has been determined using NMR spectroscopy (Sutcliffe M J et al (1994) Nature Struct Biol 1: 802–807). The structure contains a core similar to that of short chain neurotoxins, but with a novel arrangement of loops and a solvent-exposed RGD-motif. Dendroaspin is thus an integrin antagonist with a well defined fold different from that of the disintegrins, based on the neurotoxin scaffold.

The structure of dendroaspin consists of a core region from which three loops, denoted I, II and III (residues 4–16, 23–36 and 40–50 of SEQ ID NO:4) extend outwards (FIG. 1). The core contains the four disulphide bonds which are spatially close to each other and hold the loops together. The amino acid sequence of dendroaspin (SEQ ID NO:1) is shown in FIG. 2A.

In the following examples materials used include:

Restriction enzymes, T4 polynucleotide kinase, T4 DNA ligase, IPTG (isopropyl-β-D-thio-galactopyranoside) and DH5α competent cells purchased from Life Technologies Ltd (UK) or Promega Ltd (Southampton, UK). Vent (exo-) DNA polymerase was supplied by New England Biolabs Ltd (Hitchin, UK). Oligonucleotides were made either in King's College School of Medicine & Dentistry (London, UK) or by Cruachem Ltd (Glasgow, UK) and further purified by denaturing PAGE on a 15% acrylamide/8 M urea gel. Deoxynucleotide triphosphates (dNPT's), dideoxynucleotide triphosphates (ddNTP's) and plasmid pGEX-3X, a vector that expresses a cloned gene as a fusion protein linked to glutathione S-transferase (GST) and Glutathione-Sepharose CL-4B were purchased from Pharmacia Biotech Ltd (Herts, UK). "Geneclean" kit and Plasmid maxi kit were purchased from Bio 101 (La Jolla Calif., USA) and Qiagen Ltd (Surrey, UK) respectively. The sequencing Sequenase 2.0 was obtained from Cambridge Bioscience (Cambridge, UK). $[^{35}S]$dATP[αS] and $^{125}I$ (15.3 mCi/mg iodine) were supplied by NEN Dupont (Herts, UK) and Amersham International Plc (Amersham, Bucks, England) respectively.

EXAMPLE 1

Construction of Expression Vectors Encoding Variants of Dendroaspin

The wild type dendroaspin gene was inserted into a plasmid pGEX-3X (FIG. 2) successfully and expressed according to the method of Lu et al, (1996) J Biol Chem 271: 289–295. Starting with the wild type gene for dendroaspin, variants of dendroaspin genes were engineered using recombinant DNA technology. For the longer insertion variants, oligo-nucleotides which encode the non-dendroaspin or heterologous amino acids were simply inserted directly into suitably restriction digested wild type dendroaspin gene and then ligated. For minor changes such as modification of a few amino acid residues including the insertion, substitution or deletion, the Transformer™ Site-Directed Mutagenesis kit from Clonetech Laboratories was used in accordance with the manufacturers instructions.

FIG. 2A shows the nucleotide sequence of the synthetic dendroaspin (Den) gene (SEQ ID NO:2). The gene was designed on the basis of the known amino acid sequence (Williams J A et al ((1992)) Biochem Soc Trans 21: 73S) and the codons for each amino acid were adopted from those which were highly expressed in *E coli* (Fiers W ((1982)) Gene 18: 199–209) Ten synthetic oligonucleotides are shown in brackets and numbered individually 1 to 10 either above the coding strand or below the non-coding strand. The stop codon is indicated by an asterisk. Three-letter amino acid code is used and the total of 59 amino acids of Den are only numbered 1 for N-terminal residue arginine and 59 for C-terminal leucine.

FIG. 2B is a partial restriction map of pGEX-DEG. Only the dendroaspin (Den)gene and its relevant upstream region are shown.

FIG. 3A shows the amino acid sequences of various modified dendroaspin molecules (SEQ ID NOS:5–22) which will be described in more detail below. In each case the modified inserted residues are set out beneath the amino acid sequence of dendroaspin (SEQ ID NO:4).

EXAMPLE 2

Modified Dendroaspin Containing a Platelet-derived Growth Factor (PDGF) Domain Platelet-derived growth factor (PDGF) is a 30-kDa polypeptide and a major serum mitogen and chemotactic factor for mesenchymal cells. Originally purified from human platelets, PDGF has subsequently been found to be produced by other cell types such as smooth muscle cells, placental cytotrophoblast cells, fibroblasts and connective tissue. PDGF has been shown to promote cell migration and proliferation and these are key events in natural processes such as embryogenesis and wound healing. PDGF has also been implicated in a number of pathological states, such as arteriosclerosis, fibrosis and rheumatoid arthritis (Heldin C H and Westermark B (1990) Cell Regul 1: 555–566 and Engstrom U et al (1991) J Biol Chem 267: 16581–16587). PDGF is a dimer of two similar chains called A- and B-chains.

Amino acid sequences derived from PDGF B chain is inserted into loop II of dendroaspin as shown in FIGS. 3A (SEQ ID NOS:6–10) and 3C (SEQ ID NO:7), maintaining the adhesive property of the RGD sequence of loop III within dendroaspin. The modified dendroaspins are then examined for competitive inhibition of PDGF activity by analyzing smooth muscle and fibroblast cell proliferation and integrin antagonist activity. FIG. 3D summarizes the results obtained with the example given in FIG. 3C. The modified dendroaspin molecules inhibit ADP-induced platelet aggregation and PDGF-induced proliferation of fibroblast cells.

Assembly and cloning of the gene of dendroaspin containing PDGF loop I: The gene of dendroaspin containing PDGF loop I was assembled from the fragments (77 mer, 76 mer, 42 mer and 44 mer) of wild-type gene, after digestion with Bam HI, EcoR I, Hinf I and Hpa II, and a pair of complementary phosphorylated mutagenesis oligos (81 mer and 80 mer). A mixture of the total 6 fragments was heated to 85° C. for 5 min and annealed by slowly cooling down to room temperature (RT). Ligation was performed at 16° C. for 15 hours in a total volume of 50 μl containing about 1 mM of each fragment, 50 mM Tris-HCl (pH7.6), 10 mM $MgCl_2$, 1 mM DTT, 1 mM ATP and 5% PEG 8000 and 5 units of T4 ligase. After ligation, 1 μl of ligation mixture was used as template together with two 5'-overhanging oligonucleotides as primers and 2 units of Vent polymerase for PCR. The single product obtained was of expected size checked by 2% agarose gel. The hybridisation gene was then cloned into the vector pGEX-3X to produce the recombinant plasmid pGEX-3X comprising PDGF-niodified dendroaspin gene.

Transformation and plasmid DNA isolation: The pGEX-3X vector comprising the PDGF-modified dendroaspin gene (about 5 ng) was used to transform 50 μl of the *E coli* strain DH5α. controls were set up of a vial containing competent cells only, a vial containing unligated plasmid DNA and a vial containing wild-type plasmid DNA. The incubation media used for the bacteria is SOC medium (containing 20 g/l bacto-tryptone, 5 g/l bacto-yeast extract, 0.5 gl NaCl, 2.5 mM KC, 20 μM $MgCl_2$ and 20 mM glucose). The transformation step was followed by a recovery period in which the bacterial culture was incubated without ampicillin for an hour. After transformation, a sufficient quantity of each of the bacterial cultures was plated out. SOC agar medium containing ampicillin was used to culture the bacteria. The ampicillin selection marker of pGEX-3X confers ampicillin resistance on any transformed bacteria allowing them to grow whilst any untransformed bacteria are eliminated. The control plate remained clear following incubation overnight.

Individual colonies were picked from the plates, each one representing a modified dendroaspin gene. These were cultured on SOC media containing ampicillin for a few hours. A small amount of each was removed and transferred to new SOC media containing ampicillin. Sterile glycerol was added to the original bacterial culture to permit storage at −70° C. as a stock supply. The remaining cultures we re incubated overnight. The isolation of the plasmid DNA from the transformed bacterial culture is carried out by a plasmid mini prep (for quick test) or maxi-prep (for DNA sequencing) following the manufacturer's instructions (QIAGEN). A plasmid mini-prep was carried out on each to isolate the plasmid DNA once more; the majority of which comprised the modified dendroaspin gene. DNA sequencing was carried out on the region of the plasmid containing the dendroaspin gene fragment to check that the modification was present and correct. Complete DNA sequencing of the inserted fragments was made using the dideoxy chain-termination method of Sanger et al (1977) Proc Natl Acad Sci 74: 5463–5467.

Protein expression: *E coli* DH5α was transformed with modified plasmid pGEX-3X using standard methods particularly as described in Sambrook et al (1989) Molecular cloning: A Laboratory Manual, Cold Spring Harbor Laboratory Press, N.Y. The transformed cultures were used for protein expression. Medium were inoculated with an overnight seed culture (1%, v/v) and grown in LB/ampicillin medium (100 μg/ml) and shaken at 37° C. until an $A_{600}$ of 0.7 was obtained. IPTG was then added to a final concentration of 0.1 mM for induction. The cells were grown for an additional 4 hours at a lower temperature of 30° C. and harvested by centrifugation.

Purification of fusion protein: Recombinant dendroaspins were purified as follows by suspending the cell pellets in phosphate buffered saline (PBS) buffer (pH 7.4) containing 1% Triton X-100 and the protease inhibitors phenylmethylsulfonyl fluoride (1 mM), pepstatin (1 μM), aprotinin (2 μg/ml), trypsin inhibitor from soyabean (1 μg/ml), 1 mM EDTA, and sonicated on ice. The sonicated mixture was centrifuged at 7,800× g at 4° C. for 10 min to pellet the cell debris and insoluble material. Recombinant GST-dendroaspin and GST-modified-dendroaspins from supernatants were purified by affinity chromatography on glutathione-Sepharose CL-4B columns by adsorption in PBS containing 150 mM NaCl and elution with 50 mM Tris-HCl containing 10 mM reduced glutathione (pH 8.0). Elution of the adsorbed material with glutathione (pH 8.0) resulted in the appearance of a major band migrating at 32 kDa (GST-dendroaspin fusion protein) in polyacrylamide gels. (FIGS. 5A and 5B).

The appropriate fractions comprising the 32-kDa fusion proteins were then digested in the presence of 150 mM NaCl, 1 mM $CaCl_2$, and Factor Xa (1:100, w/w, Factor Xa:fusion protein) at 4° C. for 24 h. Treatment of the purified GST-proteins with Factor Xa released recombinant proteins migrating as 7-kDa bands (FIG. 5C), approximating the size of dendroaspin, and free GST appearing as an intensification of a 28-kDa band on SDS-polyacrylamide gel electrophoresis. The digested mixture was loaded onto a Vydac $C_{18}$ reverse-phase HPLC analytical column (TP104) and eluted with a linear gradient of 0–26% acetonitrile (1.78% per min) containing 0.1% trifluoroacetic acid, followed by 26–36% acetonitrile in 0.1% trifluoroacetic acid (0.25% per min). When necessary, further analytical columns were run under the same conditions. FIGS. 6A and 6B show the elution profile of reverse phase HPLC runs.

Western blotting: Fusion proteins (10 μg) were electrophoresed on an SDS-PAGE (12%) gel and transferred by semi-dry blotting to nitrocellulose membranes using a current density of 0.8 $mA/cm^2$. The nitrocellulose membranes were blocked for 2 h at RT with 5% dried milk in TBS/Tween buffer (20 mM Tris, 500 mM NaCl, 0.1% Tween) following which they were probed with a corresponding primary antibody overnight and then with either anti-rabbit or anti-mouse second antibody linked to horseradish peroxidase for 2 h. The blots were then developed with aminoethylcarbazole (FIG. 7).

Production of R51 antibody: Peptide 1 (linear amino acid sequence of PDGF loop) was conjugated to bovine thyroglobulin (Tg) via rabbit serum albumin (RSA), via the thiol group, using the hetero-bifunctional crosslinkers, sulfphosuccinimidyl 4-(N-maleimidomethyl) cyclohexane-1-carboxylate (Sulpho-SMCC) and γ-maleimidobutyrate succinimide (GMBS), respectively. The manufacturer's own procedure was used. The conjugates were made 1 mg/ml in PBS and stored at −20° C.

New Zealand white rabbits were immunised with Tg-peptide 1 (100 μg of each per rabbit injected subcutaneously in 1 ml of 1:1 PBS:Freund's Complete Adjuvant). The rabbits were boosted after 6 and 12 weeks using the same dose but in Freund's Incomplete Adjuvant. Final bleeds were taken 10 days after the last booster injection. The antisera were aliquoted and stored at −20° C.

Production of R38 and R65 antibodies: IgG (R38 and R65) was purified from the above-mentioned antisera using Protein-G affinity chromatography (Hi-TRAP Protein-G, Pharmacia, Upsala, Sweden) as described by the manufacturers. Purity was checked by SDS-PAGE. The IgG solutions in PBS were filter sterilised, aliquoted and stored at −20° C.

EXAMPLE 3

Identification of RGD Function (Dendroaspin Activity)

Platelet aggregation: Platelet aggregation was measured by the increase in light transmission as described in Lu et al (1994) Biochem J 304: 929–936 and used to identify RGD function. Briefly, platelet rich plasma (PRP) was prepared from citrated human blood from healthy individuals by centrifugation at 200 g for 15 min. Platelets were prepared from PRP by centrifugation at 1200 g for 15 min. The pellets were washed and resuspended in adhesion/aggregation buffer (145 mM NaCl, 5 mM Kcl, 1 mM $MgCl_2$, 2 mM $CaCl_2$, 10 mM glucose, 3.5 mg/ml BSA and 10 mM HEPES, pH 7.35) and adjusted to a count of $3\times10^8$/ml. Platelet aggregation (320 μl incubations) was induced with 10 μM ADP in the presence of 1.67 mg/ml fibrinogen and measured using a Payton Dual-Aggregometer linked to a chart recorder.

Platelet adhesion: Platelet adhesion was also measured as described to further identify RGD function as described in Lu et al (1994) supra. Briefly, 96 well plates were coated overnight at 4° C. with either human fibrinogen or fibronection reconstituted in PBS (pH 7.4) at appropriate concentrations (2–10 μg/ml, 100 μl volumes). Platelets were treated with antagonists at appropriate concentrations for 3 min before addition of 90 μl of the mixtures to the microtitre plates which were pre-loaded with 10 μl of 500 μM ADP giving a final concentration of 50 μM and the number of adherent platelets was determined by measuring endogenous acid phosphatase using 130 μl/well of developing buffer (sodium acetate, 10 mM p-nitrophenyl phosphate, 0.1% Triton X-100, pH 5.5) and read at 410/630 nm on an automated plate reader.

Iodination studies of ligands and ligand binding assays: Iodination of all variants of dendroaspin was performed using Enzymobead Radioiodination Reagent (Biorad Laboratories) according to the manufacturer's instructions. The binding of $^{125}$I-labelled disintegrins, dendroaspin and modified dendroaspins to washed platelets was performed under equilibrium conditions essentially as described previously in Lu et al (1994) supra. The incubation mixture contained 300 $\mu$l of washed platelets (3×10$^8$/ml), 10 $\mu$l agonist (1.75 mM ADP giving a final concentration 50 $\mu$M), 10 $\mu$l $^{125}$I-labelled protein samples, 5–20 $\mu$l resuspension buffer and was made up to a final volume of 350 $\mu$l. In antibody inhibition studies, platelet suspensions were treated with antibody for 30 min prior to exposure to ADP and then the $^{125}$I-protein samples added and the mixture was incubated at RT for a further 60 min. Incubations were terminated by loading the mixture onto a 25% (w/v) sucrose, 1% BSA cushion and centrifugation at 12,000 g for 10 min. Both platelet pellets and supernatants were counted to determine the levels of bound and free ligand. Background binding levels were determined in the presence of a 50-fold excess of cold protein samples or disintegrin or 10 mM EDTA.

Identification of grafted loops: Identification of the functions of a grafted loop is dependent on the function of the parent proteins of the grafted loop.

EXAMPLE 4

Assays for Effects of PDGF Loop I in Dendroaspin

Competition ELISAs (CELIA): The relevant quantity of Den-PDGF, or PDGF as competitors were added simultaneously with appropriately diluted rabbit anti-PDGF antiserum and incubated for 2 h. Each rabbit anti-serum was used at a dilution within the linear part of the standard direct ELISA curve and gave an OD of 1.2 to 1.5 at 405 nm, after a 30 min incubation with substrate, when assayed against the appropriate RSA-peptide conjugate.

Cell culture and [$^3$H]-thymidine incorporation assay: Human dermal foreskin fibroblasts (used between passage number 7–10) were maintained in complete DMEM containing 10% FBS. Sub-confluent monolayers from 75 cm$^3$ tissue culture flasks were trypsinized, counted and seeded into 24 well (Costar) or 48 well (Falcon) flat bottom tissue culture plates at cell densities of 10,000 cells/well, and grown until approximately 65% confluent (2 days). Cells were rendered quiescent by replacing the medium with complete DMEM containing 0.2% or 0.5% FBS for 48–72 h. All cell cultures were performed at 37° C. in a humidified atmosphere containing 8% $CO_2$ in air.

Inhibition of growth factor induced cellular proliferation was brought about by replacing the medium, at time zero, with complete DMEM containing varying concentrations of the Den-PDGF and peptide P1 (linear sequence of PDGF domain), respectively. The PDGF concentration for induction was used at a range of 10–20 ng/ml.

[$^3$H]-thymidine (0.3 mCi/c100 $\mu$l/well) was added after 20 h–22 h and incubated until hours 27.5–28. Medium was aspirated, cells were washed twice with cold PBS and fixed by the addition of 500 $\mu$l 10% TCA and incubated for 30 min at 4° C. Cells were next washed once with 0.5 ml 70% ethanol and stored at −20° C. Cells were then solubilised by addition of 500 $\mu$l of 0.1 N NaOH to each well for 30 min at room temperature. Cellular incorporated [$^3$H]-thymidine was quantified by scintillation counting of a 400 $\mu$l sample from each well. The percentage of inhibition of cellular proliferation was worked out as:

$$\frac{([^3H]\text{ – thymidine incorporated with PDGF}) - ([^3H]\text{ – thymidine incorporated with PDGF} + M^*\text{ or Pl})}{([^3H]\text{ – thymidine incorporated with PDGF}) - ([^3H]\text{ – thymidine incorporated with 0.2\% FCS})} \times 100$$

$M^*$: denotes modified dendroaspins

FIG. 8 shows that the results of tests in which PDGF-dendroaspin inhibits PDGF-induced proliferation by 10–34% (there was no inhibition which has been found when using wild-type dendroaspin as a control) in the range 6.5–60 $\mu$M.

EXAMPLE 5

Modified Dendroasiin Containing a Sequence Derived From the Fifth EGF-like Domain of Thrombomodulin Thrombomodulin serves as a receptor of thrombin. Thrombin is a trypsin-like serine protease fulfilling a central role in both haemostasis and thrombosis. In the coagulation cascade, thrombin is the final key enzyme, proteolytically cleaving fibrinogen to release fibrinopeptides A and B and generating fibrin monomers which can then polymerize to form a haemostatic plug. In addition to fibrinogen cleavage, thrombin exerts a positive feedback on its own production by generating coagulation factors Va and VIIIa which act as cofactors of thrombin activation. Factor XIII is also activated by thrombin and cross-links and stabilises the fibrin polymer. Natural anticoagulant mechanisms limit these processes through inhibition by the serpin, antithrombin III and through activation of protein C by thrombin/thrombomodulin complex. Thrombomodulin is a cell receptor located on the endothelial cell surface and it binds and alters the molecular specificity of thrombin by decreasing its ability to catalyze clot formation while converting thrombin into a potent protein C activator. Activated protein C destroys factor Va and VIIIa terminating the clotting cascade. Thus, the balance between pro- and anti-coagulant mechanisms maintains the normal physiological conditions and allows the local generation of thrombin, whilst preventing it from becoming a systemic or potentially dangerous process. Moreover, thrombin also activates platelets and endothelial cells. Upon platelet activation by thrombin, platelets undergo shape change, aggregation and release their storage granule contents (eg platelet factor-4, ADP, 5-hydroxytryptamine). Thrombin also increases the synthesis and secretion of thromboxane $A_2$ and platelet activating factor. The interaction of thrombin with endothelial cells also results in the secretion of various agents (eg tissue plasminogen activator, PDGF, endothelin) as well as the acceleration of protein C activation binding to thrombomodulin which initiates protein C anticoagulant pathway.

As examples, a sequence derived from the fifth epidermal growth factor (EGF) like domain of thrombomodulin was grafted into dendroaspin. The thrombin binding affinity of the novel protein was determined on the basis of inhibition of fibrinogen clotting.

An appropriate plasmid expression vector was made according to the procedures of Example 1 except that a thrombomodulin domain was inserted into dendroaspin as shown in FIG. 3A (SEQ ID NO:14) where the sequence grafted into loop II of dendroaspin is shown.

Expression, isolation and purification of the TM-modified dendroaspin was also performed in accordance with Example 1 and the RGD function of the modified proteins tested as described in Example 2.

Human thrombomodulin has Mr about 100 kDa and consists of an N-terminal domain that is homologous to the family of C-type Lectins, six tandemly repeated epidermal growth factor (EGF)-like domains, a Ser/Thr rich domain, a transmembrane domain, and a short cytoplasmic tail. In a particular example shown in FIG. 3C (SEQ ID NO:44), we have inserted a sequence derived from the fifth EGF-like domain of thrombomodulin into dendroaspin and made additional modifications of appropriate parts of the dendroaspin to prevent the steric hindrance which causes loss of its biological functions.

As indicated in FIG. 3D the modified dendroaspin molecules have ADP- and thrombin-induced platelet aggregation activities and they also prolongs the thrombin clotting time.

EXAMPLE 6

Assays for Effects of Thrombomodulin Domain in Dendroaspin

Thrombin-induced fibrinogen clotting time: Thrombin-induced fibrinogen clotting time was determined using an Amelung KC-10 instrument as follows. 50 $\mu$l of thrombin (3.3 $\mu$g/ml) in 50 mM Tris-HCL, pH7.5, containing 150 mM NaCl and 5 mM $CaCl_2$ was mixed with 10 $\mu$l of various concentrations of both modified (Den-TM) and wild type dendroaspin (as a control for comparison). After a 2 min incubation at 37° C., 100 $\mu$l of fibrinogen (160 $\mu$g/ml) in the same buffer was added to determine the clotting time.

Protein C activation: To check whether the Den-TM has any influence on protein C activation a two stage assay was used as described by Tsiang et al (1990) Biochemistry 29: 10602–10612. In the first stage, thrombin and protein C were added to suitable final concentrations in a reaction volume of 110 $\mu$l, with or without wild-type or mutant dendroaspins with either 2 mM $CaCl_2$ or 1 mM $Na_2$ EDTA. Reaction mixtures were incubated for 30 min and stopped by addition of antithrombin III and heparin. The active protein C generated was assayed by hydrolysis of substrate S-2366.

Thrombin-induced platelet aggregation: Thrombin-induced platelet aggregation in washed platelets for both wild-type and mutant dendroaspins were determined as described in Example 3 above, except thrombin was used as an agonist.

Thrombomodulin binding: Thrombomodulin binding was performed as described by Tsiang et al (1990) supra.

EXAMPLE 7

Modified Dendroaspin Containing a Sequence Derived from Glycoprotein (GP) IB Glycoprotein (GP) IB$\alpha$ is required for expression of the high affinity $\alpha$-thrombin binding site on platelets (Marco et al (1994) J Biol Chem 269: 6478–6484). This function may be of crucial importance in the initiation of haemostasis and thrombosis and may play a role in the development of pathological vascular occlusion. A modified dendroaspin was engineered which contains a sequence derived from GP IB to create both thrombin and integrin antagonist activities.

An appropriate plasmid expression vector was made as described in Example 1, except that a glycoprotein IB$\alpha$ domain was inserted into loop I of the dendroaspin molecule as shown in FIGS. 3A (SEQ ID NOS:11, 15 & 16) and 3C (SEQ ID NO:45) where the amino acid residues of the grafted domain are aligned with the full amino acid sequence of dendroaspin.

As summarized in FIG. 3D, the modified dendroaspin molecules inhibit thrombin activity and platelet aggregation.

Assembly and cloning of the gene of dendroaspin containing glyocoprotein IB (GP IB) domain: The gene of dendroaspin containing GP IB domain was assembled from the fragments (81 mer, 82 mer, 42 mer and 44 mer) of wild-type gene, after digestion with Bam HI, EcoR I, Hinf I and Hpa II, and a pair of phosphorylated mutagenesis oligos (83 mer and 82 mer). The experimental procedures of annealing, ligation, PCR and assembling were similar as described previously for Den-PDGF.

Expression, isolation and purification of the GP IB$\alpha$-modified dendroaspin was performed as described in Example I and the RGD function of the molecule assayed in accordance with Example 3.

EXAMPLE 8

Assays for Effects of the GP IB Domain in Dendroaspin

Measurement of thrombin binding to platelets: Thrombin binding to washed platelets was measured in a calcium-free aggregation/adhesion buffer (see measurement of platelet aggregation in example 3). Washed platelets were equilibrated at 37° C. for 10 min before the assay and then incubated with $^{125}$I-$\alpha$-thrombin for 10 min at 25° C. Binding as a function of ligand concentration was determined with a constant concentration (0.1 nM) of $^{125}$I-$\alpha$-thrombin mixed with increasing concentrations (between 1 and 200 nM) of unlabeled $\alpha$-thrombin. The binding was initiated by the addition of platelets to the thrombin mixture. Platelets and bound thrombin were separated from unbound thrombin after 10 min incubation by centrifugation through a layer of 20% sucrose at 12000 g for 4 min (Lu et al (1994) supra).

The effect of dendroaspin containing GP IB domain on thrombin binding to platelets was evaluated by mixing varying concentrations of the mutants with the washed platelets and adding a constant concentration of $^{125}$I-$\alpha$-thrombin. The results were analyzed as described previously (Lu et al (1996) supra).

Measurement of platelet aggregation and secretion: The release of ATP from the dense granules of platelets was measured by the luciferin-luciferase assay. Washed platelets were resuspended in 0.4 ml calcium-free aggregation/adhesion buffer at a count of $2.5\times10^8$/ml, aliquots of 0.4 ml were measured using a lumiaggregometer (Chrono-Log Corp). 50 $\mu$l of luciferin-luciferase reagent was then added, followed by a-thrombin at the final concentration of 0.26 nM; the ensuing release of ATP was determined by recording the change in luminescence, using a lumiaggregometer (Chrono-Log Corp). Platelet aggregation was measured as described in Example 3 above. To test the inhibitory effect of mutant dendroaspin containing GP IB domain on ATP release and platelet aggregation, mutant proteins were added and mixed with platelets for 5 min at 37° C. before addition of luciferin/luciferase and thrombin.

Amidolytic activity of thrombin and clotting of fibrinogen: Amidolytic activity of thrombin and clotting of fibrinogen was determined as described in Example 10 below.

EXAMPLE 9

Modified Dendroaslin Containing a Domain of Hirudin

Hirudin, a potent thrombin inhibitor from the bloodsucking leech *Hirudo medicinalis*, is a single polypeptide chain protein containing 65 amino acid residues (Maraganore et al (1989) J Biol Chem 264: 8692–8698). We produced a modified dendroaspin which includes amino acid residues Asn$^{52}$–Leu$^{64}$, or Phe$^{45}$–Gln$^{65}$ from hirudin. The new construct contains both anti-thrombin binding and platelet anti-adhesive domains.

The plasmid expression vector was made as described in Example 7, except that further mutation site has been made for a minor change corresponding to the amino acid residues PRP in loop II of dendroaspin. For the minor changes, the Transformer™ Site-Directed mutagenesis kit from Clonetech Laboratories was used. The experimental procedures were performed according to manufacturer's instructions except that the hirudin domain was grafted into loops I and II of dendroaspin. The modified molecules are shown in FIGS. 3A (SEQ ID NOS:12–13, 17–19) and 3C (SEQ ID NO:43) where the hirudin-derived amino acid residues are aligned with the native dendroaspin sequence. FIG. 3D indicates how the molecule of FIG. 3C (SEQ ID NO:43) delays thrombin clotting time and inhibits ADP or thrombin induced platelet aggregation.

Expression, isolation and purification of the Den-HR was essentially as described in Example 1. The RGD function of the molecule was established according to the assay methods of Example 3.

EXAMPLE 10

Assays for Effects of Hirudin Domain in Dendroasdin

Amidolytic activity of thrombin and clotting of fibrinogen: The amidolytic activity of α-thrombin was performed using the chromogenic substrate S-2238 (Chromogenix) and α-thrombin at a final concentration of 0.06 unit/ml. Thrombin releases p-nitroaniline from the substrate and the rate of this reaction was monitored in microtiter plates at 405 nm using an automated spectrophotometer (Autoreader III, Ortho Diagnostic Systems). The inhibitory effect of Den-HR on thrombin cleavage of the chromogenic substrate was measured at final concentration between nM–mM. Thrombin and Den-HR were premixed and reactions were initiated by the addition of substrate. To evaluate the fibrinogen clotting activity 200 μl of α-thrombin (final concentration, 1 nM) in 0.05 M Na phosphate, pH 6.5 (BSA, final concentration, 1%) was incubated for 5 min at RT and then 200 μl of normal plasma was added containing 0.011 M trisodium citrate as anticoagulant. The time to observe the start of fibrinogen clotting (thrombin time) was measured using an automated coagulometer at 37° C. The effect of mutants on fibrinogen clotting by α-thrombin was determined by substituting the HEPES buffer in the first mixture with mutants at a range of concentrations.

EXAMPLE 11

Modified Dendroaspin Containing a Thrombin-based Pentide which Blocks the Procoagulant Activity of Thrombin The binding site for thrombomodulin within human thrombin has been localized to a region in the B-chain of thrombin. Its sequence was introduced into dendroaspin as shown in FIG. 3C (SEQ ID NO:46) to generate a bifunctional molecule which blocks thrombin procoagulant activities and also inhibit ADP/thrombin-induced platelet aggregation. Functional characterization of this mutant includes the measurement of thrombin-induced fibrinogen clotting time as described in Example 6 and the measurement of platelet aggregation induced by ADP/thrombin as described in Examples 3 and 6 above. FIG. 3D summarizes the properties of the bifunctional molecule as being able to delay thrombin clotting and inhibits platelet aggregation induced either by ADP or thrombin.

In the case of the molecules of FIG. 3C (SEQ ID NOS:43–46, 7), modification of the loops has become necessary due to a steric effect caused by the introduction of "foreign" sequence, e.g. when a sequence derived from PDGF introduced into dendroaspin, anti-PDGF activity was generated, but the anti-platelet activity was lost. This steric effect was designed out by the introduction of a similar RGD-loop as the loop III of dendroaspin into loop I. The sequences of engineered molecules based on dendroaspin scaffold and their functions are summarized in following Table 1 and FIG. 1 respectively.

EXAMPLE 12

Site Directed Mutaaenesis of Modified Dendroaspins

Each of the modified dendroaspins described above can be modified around the RGD loop or any other portion of the molecule as is desired by way of site directed mutagenesis. Procedures used are as described in Lu et al (1996) supra. Possible RGD flanking region modifications are shown in FIG. 3B (SEQ ID NOS:23–42) together with the results of dendroaspin activity assays. Some modifications increase activity whereas other modifications negate activity.

EXAMPLE 13

Antithrombotic Activity of Modified Dendroaspins in a Guinea Pig Arterial Thrombosis Model The four modified dendroaspins produced in the above Examples can be tested for antithrombotic activity in vivo in a guinea pig model for arterial thrombosis as described in detail by Carteaux J P et al (1995) Circulation 91: 1568–1574. A range of doses of each modified dendroaspin in the range 0.1 mg/kg of body weight to 1 mg/kg can be administered separately to animals by intravenous infusion. Control tests of 50–150 IU/kg heparin and placebo can be carried out in parallel.

EXAMPLE 14

Activity of Modified Dendroaspins on Cellular Proliferation Following Arterial Injury in a Rabbit Athersclerosis Model Den-PDGF, Den-TM, Den-GP and Den-HR can be tested in the rabbit in an in vivo model system as described by Ragosla M et al (1996) Circulation 93: 1194–1200. After induction of athersclerosis, rabbits can be infused intravenously with a dosage of 0.1 mg–0.5 mg/kg of these modified dendroaspins. A first set of control animals were treated intra-arterially with a single bolus of heparin (150IU/kg). A second control set of animals can be set up to receive saline instead of modified dendroaspins. Balloon angioplasty is then performed on test and control animals and followed by quantitative angiography, measurement of activated partial thrombosplastin time (aPTT), $^{3}$H-thymidine incorporation into the injured artery and follow up studies of luminal narrowing.

EXAMPLE 15

Thrombolytic Activity of Modified Dendroaspins Tested in an in vivo Pig Model System The model system of Mruk J S et al (1995) Circulation 93: 792–799 can be employed. Pigs with occlusive thrombi may be administered intravenously with 0.1 mg–1 mg/kg of the modified dendroaspins mentioned in Example 12 above. A dose of heparin or hirudin (bolus of 100 IU/kg followed infusion of 20 IU/kg) can be administered to control animals. Animals receiving only saline serve as controls.

What is claimed is:

1. A hybrid dendroaspin-based polypeptide comprising (a) an amino acid sequence having platelet-binding activity, said amino acid sequence comprising the tripeptide sequence Arg-Gly-Asp (RGD), and (b) at least one additional amino acid sequence selected from the group consisting of: platelet derived growth factor (PDGF), glycoprotein IBα, hirudin, thrombomodulin, vascular epidermal growth factor, transforming growth factor-β1, basic fibroblast growth factor, angiotensin II, factor VIII and von Willebrand factor.

2. A polypeptide as in claim 1 comprising an amino acid sequence selected from the group consisting of SEQ ID NO: 5, SEQ ID NO: 6, SEQ ID NO: 7, SEQ ID NO: 8, SEQ ID NO: 9, and SEQ ID NO: 10.

3. A hybrid dendroaspin-based polypeptide comprising (a) an amino acid sequence having platelet-binding activity, said amino acid sequence comprising the tripeptide sequence Arg-Gly-Asp (RGD), and (b) at least one additional amino acid sequence having platelet binding activity.

4. A hybrid dendroaspin-based polypeptide as in claim 1, wherein said at least one additional amino acid sequence has anticoagulant activity.

5. A hybrid dendroaspin-based polypeptide as in claim 1 or claim 3, wherein said at least one additional amino acid sequence inhibits clotting.

6. A hybrid polypeptide comprising (a) a dendroaspin scaffold having integrin-binding activity and (b) at least one non-wild-type dendroaspin domain, wherein said at least one non-wild-type dendroaspin domain is selected from the group consisting of platelet derived growth factor (PDGF), glycoprotein IBα, hirudin, thrombomodulin, vascular epidermal growth factor, transforming growth factors β1, basic fibroblast growth factor, angiotensin II, factor VIII and von Willebrand factor.

7. A hybrid polypeptide comprising (a) a dendroaspin scaffold having integritin-binding activity and (b) at least one non-wild-type dendroaspin domain, said at least one non-wild-type dendroaspin domain conferring platelet binding activity.

8. A hybrid polypeptide as in claim 7 wherein said at least one non-wild-type dendroaspin domain is divided into two portions separated by at least one amino acid residue of said dendroaspin scaffold.

9. A hybrid polypeptide as in claim 7, comprising at least two non-wild-type dendroaspin domains.

10. A hybrid polypeptide as in claim 9, wherein said at least two non-wild-type dendroaspin domains are the same.

11. A hybrid polypeptide comprising (a) a dendroaspin scaffold having integrin-binding activity and three structural loops comprising loop I, loop II and loop III, said integrin-binding activity being conferred by loop III, and (b) a non-wild-type dendroaspin domain which is incorporated into a region external to said loops and augments the native dendroaspin amino acid residues in said region and which confers anticoagulant activity.

12. A hybrid polypeptide as in claim 11 wherein said loop III is modified as compared with native dendroaspin by insertion, deletion or substitution of between one and eight amino acids.

13. A hybrid dendroaspin-based polypeptide comprising (a) an amino acid sequence having platelet-binding activity, said amino acid sequence comprising the tripeptide sequence Arg-Gly-Asp (RGD), and (b) at least one additional amino acid sequence having anticoagulant activity.

14. A hybrid dendroaspin-based polypeptide comprising (a) an amino acid sequence having platelet-binding activity, said amino acid sequence comprising the tripeptide sequence Arg-Gly-Asp (RGD), and (b) at least one additional amino acid sequence having antithrombotic activity.

15. A hybrid dendroaspin-based polypeptide comprising (a) an amino acid sequence having platelet-binding activity, said amino acid sequence comprising the tripeptide sequence Arg-Gly-Asp (RGD), and (b) at least one additional amino acid sequence having cell migration inhibiting activity.

16. A hybrid dendroaspin-based polypeptide comprising (a) an amino acid sequence having platelet-binding activity, said amino acid sequence comprising the tripeptide sequence Arg-Gly-Asp (RGD), and (b) at least one additional amino acid sequence having clotting inhibiting activity.

17. A hybrid dendroaspin-based polypeptide comprising (a) an amino acid sequence having platelet-binding activity, said amino acid sequence comprising the tripeptide sequence Arg-Gly-Asp (RGD), and (b) at least one additional amino acid sequence having signal transduction regulating activity.

18. A hybrid polypeptide comprising (a) a dendroaspin scaffold having integrin-binding activity and (b) at least one non-wild-type dendroaspin domain, said at least one non-wild-type dendroaspin domain conferring anticoagulant activity.

19. A hybrid polypeptide comprising (a) a dendroaspin scaffold having integrin-binding activity and (b) at least one non-wild-type dendroaspin domain, said at least one non-wild-type dendroaspin domain conferring cell migration inhibiting activity.

20. A hybrid polypeptide comprising (a) a dendroaspin scaffold having integrin-binding activity and (b) at least one non-wild-type dendroaspin domain, said at least one non-wild-type dendroaspin domain conferring cell proliferation inhibiting activity.

21. A hybrid polypeptide comprising (a) a dendroaspin scaffold having integrin-binding activity and (b) at least one non-wild-type dendroaspin domain, said at least one non-wild-type dendroaspin domain conferring clotting inhibiting activity.

22. A hybrid polypeptide comprising (a) a dendroaspin scaffold having integrin-binding activity and (b) at least one non-wild-type dendroaspin domain, said at least one non-wild-type dendroaspin domain conferring signal transduction regulating activity.

23. A hybrid dendroaspin-based polypeptide as in any of claims 53, 13, 14, 15, 16, or 17, wherein said polypeptide has three structural loops I, II and III, and wherein said amino acid sequence having platelet-binding activity comprises the tripeptide sequence Arg-Gly-Asp (RGD) in said loop III.

24. A polypeptide as in claim 23, wherein said loop I begins after amino acid residue 4 of said polypeptide, said loop II begins after amino acid residue 23 of said polypeptide, and said loop III begins after amino acid residue 40 of said polypeptide, and wherein said at least one additional amino acid sequence is incorporated into a region external to said loops.

25. A polypeptide as in claim 24, wherein the residues in said region external to said loops are augmented by the additional amino acid sequence.

26. A polypeptide as in claim 23, wherein said at least one additional amino acid sequence is incorporated into (a) said loop I or said loop II, or (b) both said loop I and said loop II.

27. A polypeptide as in claim 23, wherein said at least one additional amino acid sequence is incorporated into (a) said loop I or said loop III, or both said loop I and said loop III.

28. A polypeptide as in claim 23, wherein said at least one additional amino acid sequence is incorporated into said loop II.

29. A polypeptide as in claim 23, wherein said loop III is modified by insertion, deletion or substitution of between one and eight amino acid residues.

30. A hybrid polypeptide as in any of claims 7, 18, 19, 20, 21, or 22, wherein said dendroaspin scaffold comprises three structural loops comprising loop I, loop II and loop III.

31. A hybrid polypeptide as in claim 30, wherein said loop I begins after amino acid residue 4 of said polypeptide, said loop II begins after amino acid residue 23 of said polypeptide, and said loop III begins after amino acid residue 40 of said polypeptide, and wherein said at least one non-dendroaspin amino acid sequence is incorporated into a region external to said loops.

32. A polypeptide as in claim 31, wherein the residues in said region external to said loops are augmented by the non-dendroaspin amino acid sequence.

33. A hybrid polypeptide as in claim 30, wherein said at least one non-wild-type dendroaspin domain is incorporated into (a) said loop I or said loop II, or (b) both said loop I and said loop II.

34. A hybrid polypeptide as in claim 30, wherein said at least one non-wild-type dendroaspin domain is incorporated into (a) said loop I or said loop III, or (b) both said loop I and said loop III.

35. A hybrid polypeptide as in claim 30, wherein said at least one non-wild-type dendroaspin domain is incorporated into said loop II.

36. A hybrid polypeptide as in claim 20, wherein said loop III comprises the tripeptide sequence Arg-Gly-Asp (RGD) and wherein said loop III is modified by insertion, deletion or substitution of one to eight amino acid residues.

37. A hybrid polypeptide as in claim 30, wherein said at least one non-wild-type dendroaspin domain is inserted into a site in the dendroaspin scaffold selected from the group consisting of between amino acid residues 2–16, 21–36, 21–31, 28–32, 9–13, or 21–33.

38. A hybrid polypeptide as in claim 30, wherein said at least one non-wild-type dendroaspin domain is inserted into the dendroaspin scaffold at the end of the dendroaspin scaffold after residue 50.

39. A method of producing a polypeptide comprising culturing a host cell transformed with a plasmid so as to express said polypeptide, extracting said polypeptide from a cell culture, and purifying said polypeptide from a cell culture extract, wherein said plasmid comprises a nucleic acid encoding the polypeptide as in anyone of claims, 3, 7, 11, 12, 13, 14, 15, 16, 17, 18, 19, 20, 21, or 22.

40. A pharmaceutical composition comprising a therapeutically effective amount of a polypeptide of any one of claims 1, 2–5, 6–10, 11–12, 13–22, 23–29, or 30–38 and a pharmaceutically acceptable excipient or carrier.

* * * * *

SEQUENCE LISTING

<160> NUMBER OF SEQ ID NOS: 48

<210> SEQ ID NO 1
<211> LENGTH: 67
<212> TYPE: PRT
<213> ORGANISM: Elapidae

<400> SEQUENCE: 1

Glu Gly Ile His Ile Glu Gly Arg Arg Ile Cys Tyr Asn His Leu Gly
  1               5                  10                  15

Thr Lys Pro Pro Thr Thr Glu Thr Cys Gln Glu Asp Ser Cys Tyr Lys
             20                  25                  30

Asn Ile Trp Thr Phe Asp Asn Ile Ile Arg Arg Gly Cys Gly Cys Phe
         35                  40                  45

Thr Pro Arg Gly Asp Met Pro Gly Pro Tyr Cys Cys Glu Ser Asp Lys
     50                  55                  60

Cys Asn Leu
 65

<210> SEQ ID NO 2
<211> LENGTH: 217
<212> TYPE: DNA
<213> ORGANISM: Elapidae
<220> FEATURE:
<221> NAME/KEY: CDS
<222> LOCATION: (2)..(199)

<400> SEQUENCE: 2 t ggg atc cat atc gaa ggt cgt cgt atc tgc tac aac cat ctt ggt act 49
Gly Ile His Ile Glu Gly Arg Arg Ile Cys Tyr Asn His Leu Gly Thr
  1               5                  10                  15 aaa ccg ccg act act gaa act tgc cag gaa gac tct tgc tac aaa aac 97
Lys Pro Pro Thr Thr Glu Thr Cys Gln Glu Asp Ser Cys Tyr Lys Asn
             20                  25                  30 atc tgg act ttc gac aac atc atc cgt cgt ggt tgc ggt tgc ttc act 145
Ile Trp Thr Phe Asp Asn Ile Ile Arg Arg Gly Cys Gly Cys Phe Thr
         35                  40                  45 ccg cgt ggt gac atg ccg ggt ccg tac tgc tgc gaa tct gac aaa tgc 193
Pro Arg Gly Asp Met Pro Gly Pro Tyr Cys Cys Glu Ser Asp Lys Cys
     50                  55                  60 aac ctt tgagaattct cgtgatga 217
Asn Leu
 65

<210> SEQ ID NO 3
<211> LENGTH: 66
<212> TYPE: PRT
<213> ORGANISM: Elapidae

<400> SEQUENCE: 3

Gly Ile His Ile Glu Gly Arg Arg Ile Cys Tyr Asn His Leu Gly Thr
  1               5                  10                  15

Lys Pro Pro Thr Thr Glu Thr Cys Gln Glu Asp Ser Cys Tyr Lys Asn
             20                  25                  30

Ile Trp Thr Phe Asp Asn Ile Ile Arg Arg Gly Cys Gly Cys Phe Thr
         35                  40                  45

Pro Arg Gly Asp Met Pro Gly Pro Tyr Cys Cys Glu Ser Asp Lys Cys
     50                  55                  60

Asn Leu

-continued

65

<210> SEQ ID NO 4
<211> LENGTH: 59
<212> TYPE: PRT
<213> ORGANISM: Artificial Sequence
<220> FEATURE:
<223> OTHER INFORMATION: Description of Artificial Sequence: modified dendroaspin

<400> SEQUENCE: 4

```
Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Met Pro Gly
         35                  40                  45

Pro Tyr Cys Cys Glu Ser Asp Lys Cys Asn Leu
     50                  55
```

<210> SEQ ID NO 5
<211> LENGTH: 60
<212> TYPE: PRT
<213> ORGANISM: Artificial Sequence
<220> FEATURE:
<223> OTHER INFORMATION: Description of Artificial Sequence: modified dendroaspin

<400> SEQUENCE: 5

```
Arg Ile Cys Phe Thr Pro Arg Gly Asp Met Pro Gly Pro Tyr Pro Gly
  1               5                  10                  15

Pro Cys Gln Glu Asp Ser Cys Tyr Lys Asn Ile Trp Thr Phe Asp Asn
             20                  25                  30

Ile Ile Arg Arg Gly Cys Gly Cys Phe Thr Pro Arg Gly Asp Met Pro
         35                  40                  45

Gly Pro Tyr Cys Cys Glu Ser Asp Lys Cys Asn Leu
     50                  55                  60
```

<210> SEQ ID NO 6
<211> LENGTH: 59
<212> TYPE: PRT
<213> ORGANISM: Artificial Sequence
<220> FEATURE:
<223> OTHER INFORMATION: Description of Artificial Sequence: modified dendroaspin

<400> SEQUENCE: 6

```
Arg Ile Cys Tyr Asn His Leu Gly Thr Lys Pro Pro Thr Thr Glu Thr
  1               5                  10                  15

Cys Gln Glu Asp Ser Cys Ile Ser Arg Arg Leu Ile Asp Arg Thr Asn
             20                  25                  30

Ala Asn Phe Leu Cys Gly Cys Phe Thr Pro Arg Gly Asp Met Pro Gly
         35                  40                  45

Pro Tyr Cys Cys Glu Ser Asp Lys Cys Asn Leu
     50                  55
```

<210> SEQ ID NO 7
<211> LENGTH: 60
<212> TYPE: PRT
<213> ORGANISM: Artificial Sequence
<220> FEATURE:
<223> OTHER INFORMATION: Description of Artificial Sequence: modified dendroaspin -continued

<400> SEQUENCE: 7

```
Arg Ile Cys Phe Thr Pro Arg Gly Asp Met Pro Gly Pro Tyr Pro Gly
  1               5                  10                  15

Pro Cys Gln Glu Asp Ser Cys Ile Ser Arg Arg Leu Ile Asp Arg Thr
             20                  25                  30

Asn Ala Asn Phe Leu Cys Gly Cys Phe Thr Pro Arg Gly Asp Met Pro
         35                  40                  45

Gly Pro Tyr Cys Cys Glu Ser Asp Lys Cys Asn Leu
     50                  55                  60
```

<210> SEQ ID NO 8
<211> LENGTH: 62
<212> TYPE: PRT
<213> ORGANISM: Artificial Sequence
<220> FEATURE:
<223> OTHER INFORMATION: Description of Artificial Sequence: modified dendroaspin

<400> SEQUENCE: 8

```
Arg Ile Cys Tyr Asn His Leu Gly Thr Lys Pro Pro Thr Thr Glu Thr
  1               5                  10                  15

Cys Gln Glu Asp Ser Cys Ile Ser Arg Arg Leu Ile Asp Arg Thr Asn
             20                  25                  30

Ala Asn Phe Leu Pro Gly Pro Cys Gly Cys Phe Thr Pro Arg Gly Asp
         35                  40                  45

Met Pro Gly Pro Tyr Cys Cys Glu Ser Asp Lys Cys Asn Leu
     50                  55                  60
```

<210> SEQ ID NO 9
<211> LENGTH: 60
<212> TYPE: PRT
<213> ORGANISM: Artificial Sequence
<220> FEATURE:
<223> OTHER INFORMATION: Description of Artificial Sequence: modified dendroaspin

<400> SEQUENCE: 9

```
Arg Ile Cys Ile Ser Arg Arg Leu Ile Asp Arg Thr Asn Ala Asn Phe
  1               5                  10                  15

Leu Cys Gln Glu Asp Ser Cys Tyr Lys Asn Ile Trp Thr Phe Asp Asn
             20                  25                  30

Ile Ile Arg Arg Gly Cys Gly Cys Phe Thr Pro Arg Gly Asp Met Pro
         35                  40                  45

Gly Pro Tyr Cys Cys Glu Ser Asp Lys Cys Asn Leu
     50                  55                  60
```

<210> SEQ ID NO 10
<211> LENGTH: 60
<212> TYPE: PRT
<213> ORGANISM: Artificial Sequence
<220> FEATURE:
<223> OTHER INFORMATION: Description of Artificial Sequence: modified dendroaspin

<400> SEQUENCE: 10

```
Arg Ile Cys Ile Ser Arg Arg Leu Ile Asp Arg Thr Asn Ala Asn Phe
  1               5                  10                  15

Leu Cys Gln Glu Asp Ser Cys Arg Lys Ile Glu Ile Val Arg Lys Lys
             20                  25                  30

Ile Ile Arg Arg Gly Cys Gly Cys Phe Thr Pro Arg Gly Asp Met Pro
```

-continued

```
        35                  40                  45

Gly Pro Tyr Cys Cys Glu Ser Asp Lys Cys Asn Leu
     50                  55                  60


<210> SEQ ID NO 11
<211> LENGTH: 61
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 11

Arg Ile Cys Gly Asp Thr Asp Leu Tyr Asp Tyr Tyr Pro Glu Glu Asp
  1               5                  10                  15

Thr Glu Cys Gln Glu Asp Ser Cys Tyr Lys Asn Ile Trp Thr Phe Asp
             20                  25                  30

Asn Ile Ile Arg Arg Gly Cys Gly Cys Phe Thr Pro Arg Gly Asp Met
        35                  40                  45

Pro Gly Pro Tyr Cys Cys Glu Ser Asp Lys Cys Asn Leu
     50                  55                  60


<210> SEQ ID NO 12
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 12

Arg Ile Cys Gly Asp Gly Asp Phe Glu Glu Ile Pro Glu Glu Tyr Leu
  1               5                  10                  15

Cys Gln Glu Asp Ser Cys Tyr Lys Asn Ile Trp Thr Phe Pro Arg Pro
             20                  25                  30

Ile Arg Arg Gly Cys Gly Cys Phe Thr Pro Arg Gly Asp Met Pro Gly
        35                  40                  45

Pro Tyr Cys Cys Glu Ser Asp Lys Cys Asn Leu
     50                  55


<210> SEQ ID NO 13
<211> LENGTH: 60
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 13

Arg Ile Cys Tyr Asn His Leu Gly Thr Lys Pro Pro Arg Pro Glu Thr
  1               5                  10                  15

Cys Gln Glu Asp Ser Cys Gly Asp Gly Asp Phe Glu Glu Ile Pro Glu
             20                  25                  30

Glu Tyr Pro Arg Pro Cys Gly Cys Phe Thr Pro Arg Gly Asp Met Pro
        35                  40                  45

Gly Pro Tyr Cys Cys Glu Ser Asp Lys Cys Asn Leu
     50                  55                  60


<210> SEQ ID NO 14
<211> LENGTH: 61
<212> TYPE: PRT
<213> ORGANISM: Artificial Sequence
```

-continued

<220> FEATURE:
<223> OTHER INFORMATION: Description of Artificial Sequence: modified
dendroaspin

<400> SEQUENCE: 14

```
Arg Ile Cys Tyr Asn His Leu Gly Thr Lys Pro Pro Thr Thr Glu Thr
  1               5                  10                  15

Cys Gln Glu Asp Ser Cys Pro Glu Gly Arg Ile Leu Asp Asp Gly Phe
             20                  25                  30

Ile Thr Asp Ile Asp Glu Cys Gly Cys Phe Thr Pro Arg Gly Asp Met
         35                  40                  45

Pro Gly Pro Tyr Cys Cys Glu Ser Asp Lys Cys Asn Leu
     50                  55                  60
```

<210> SEQ ID NO 15
<211> LENGTH: 60
<212> TYPE: PRT
<213> ORGANISM: Artificial Sequence
<220> FEATURE:
<223> OTHER INFORMATION: Description of Artificial Sequence: modified
dendroaspin

<400> SEQUENCE: 15

```
Arg Ile Cys Tyr Asn His Leu Gly Thr Lys Pro Pro Thr Thr Glu Thr
  1               5                  10                  15

Cys Gln Glu Asp Ser Cys Gly Asp Thr Asp Leu Tyr Asp Tyr Tyr Pro
             20                  25                  30

Glu Glu Asp Thr Glu Cys Gly Cys Phe Thr Pro Arg Gly Asp Met Pro
         35                  40                  45

Gly Pro Tyr Cys Cys Glu Ser Asp Lys Cys Asn Leu
     50                  55                  60
```

<210> SEQ ID NO 16
<211> LENGTH: 63
<212> TYPE: PRT
<213> ORGANISM: Artificial Sequence
<220> FEATURE:
<223> OTHER INFORMATION: Description of Artificial Sequence: modified
dendroaspin

<400> SEQUENCE: 16

```
Arg Ile Cys Tyr Asn His Leu Gly Thr Lys Pro Pro Thr Thr Glu Thr
  1               5                  10                  15

Cys Gln Glu Asp Ser Cys Gly Asp Thr Asp Leu Tyr Asp Tyr Tyr Pro
             20                  25                  30

Glu Glu Asp Thr Glu Pro Gly Pro Cys Gly Cys Phe Thr Pro Arg Gly
         35                  40                  45

Asp Met Pro Gly Pro Tyr Cys Cys Glu Ser Asp Lys Cys Asn Leu
     50                  55                  60
```

<210> SEQ ID NO 17
<211> LENGTH: 73
<212> TYPE: PRT
<213> ORGANISM: Artificial Sequence
<220> FEATURE:
<223> OTHER INFORMATION: Description of Artificial Sequence: modified
dendroaspin

<400> SEQUENCE: 17

```
Arg Ile Cys Phe Thr Pro Arg Gly Asp Met Pro Gly Pro Tyr Pro Gly
  1               5                  10                  15

Pro Cys Gln Glu Asp Ser Cys Tyr Lys Asn Ile Trp Thr Phe Asp Asn
```

-continued

```
            20                  25                  30

Ile Ile Arg Arg Gly Cys Gly Cys Phe Thr Pro Arg Gly Asp Met Pro
        35                  40                  45

Gly Pro Tyr Cys Phe Pro Arg Pro Gln Ser His Asn Asp Gly Asp Phe
    50                  55                  60

Glu Glu Ile Pro Glu Glu Tyr Leu Gln
65                  70


<210> SEQ ID NO 18
<211> LENGTH: 69
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 18

Arg Ile Cys Tyr Asn His Leu Gly Thr Lys Pro Pro Thr Thr Glu Thr
  1               5                  10                  15

Cys Gln Glu Asp Ser Cys Phe Thr Pro Arg Gly Asp Met Pro Gly Pro
            20                  25                  30

Tyr Cys Gly Cys Phe Thr Pro Arg Gly Asp Met Pro Gly Pro Tyr Cys
        35                  40                  45

Phe Pro Arg Pro Gln Ser His Asn Asp Gly Asp Phe Glu Glu Ile Pro
    50                  55                  60

Glu Glu Tyr Leu Gln
65


<210> SEQ ID NO 19
<211> LENGTH: 72
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 19

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
            20                  25                  30

Ile Arg Arg Gly Cys Gly Cys Phe Thr Pro Arg Gly Asp Met Pro Gly
        35                  40                  45

Pro Tyr Cys Phe Pro Arg Pro Gln Ser His Asn Asp Gly Asp Phe Glu
    50                  55                  60

Glu Ile Pro Glu Glu Tyr Leu Gln
65                  70


<210> SEQ ID NO 20
<211> LENGTH: 74
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 20

Arg Ile Cys Phe Thr Pro Arg Gly Asp Met Pro Gly Pro Tyr Pro Gly
  1               5                  10                  15

Pro Cys Gln Glu Asp Ser Cys Tyr Lys Asn Ile Trp Thr Phe Asp Asn
            20                  25                  30
```

-continued

```
Ile Ile Arg Arg Gly Cys Gly Cys Phe Thr Pro Arg Gly Asp Met Pro
         35                  40                  45

Gly Pro Tyr Cys Pro Gly Pro Glu Cys Pro Glu Cys Tyr Ile Leu Asp
     50                  55                  60

Asp Gly Phe Ile Cys Thr Asp Ile Asp Glu
 65                  70


<210> SEQ ID NO 21
<211> LENGTH: 70
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 21

Arg Ile Cys Tyr Asn His Leu Gly Thr Lys Pro Pro Thr Thr Glu Thr
  1               5                  10                  15

Cys Gln Glu Asp Ser Cys Phe Thr Pro Arg Gly Asp Met Pro Gly Pro
             20                  25                  30

Tyr Cys Gly Cys Phe Thr Pro Arg Gly Asp Met Pro Gly Pro Tyr Cys
         35                  40                  45

Pro Gly Pro Glu Cys Pro Glu Cys Tyr Ile Leu Asp Asp Gly Phe Ile
     50                  55                  60

Cys Thr Asp Ile Asp Glu
 65                  70


<210> SEQ ID NO 22
<211> LENGTH: 73
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 22

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Met Pro Gly
         35                  40                  45

Pro Tyr Cys Pro Gly Pro Glu Cys Pro Glu Cys Tyr Ile Leu Asp Asp
     50                  55                  60

Gly Phe Ile Cys Thr Asp Ile Asp Glu
 65                  70


<210> SEQ ID NO 23
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 23

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30
```

-continued

```
Ile Arg Arg Gly Cys Gly Cys Arg Ile Pro Arg Gly Asp Met Pro Asp
         35                  40                  45

Asp Arg Cys Cys Glu Ser Asp Lys Cys Asn Leu
     50                  55


<210> SEQ ID NO 24
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 24

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Arg Arg Ala Arg Gly Asp Asn Pro Asp
         35                  40                  45

Asp Arg Cys Cys Glu Ser Asp Lys Cys Asn Leu
     50                  55


<210> SEQ ID NO 25
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 25

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Met Pro Asp
         35                  40                  45

Asp Arg Cys Cys Glu Ser Asp Lys Cys Asn Leu
     50                  55


<210> SEQ ID NO 26
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 26

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Asn Pro Gly
         35                  40                  45

Pro Tyr Cys Cys Glu Ser Asp Lys Cys Asn Leu
     50                  55


<210> SEQ ID NO 27
<211> LENGTH: 59
<212> TYPE: PRT
```

-continued

```
<213> ORGANISM: Artificial Sequence
<220> FEATURE:
<223> OTHER INFORMATION: Description of Artificial Sequence: modified
      dendroaspin

<400> SEQUENCE: 27

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Ala Arg Gly Asp Asn Pro Gly
         35                  40                  45

Pro Tyr Cys Cys Glu Ser Asp Lys Cys Asn Leu
     50                  55


<210> SEQ ID NO 28
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 28

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Met Ala Gly
         35                  40                  45

Ala Tyr Cys Cys Glu Ser Asp Lys Cys Asn Leu
     50                  55


<210> SEQ ID NO 29
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 29

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Met Ala Gly
         35                  40                  45

Pro Tyr Cys Cys Glu Ser Asp Lys Cys Asn Leu
     50                  55


<210> SEQ ID NO 30
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 30

Arg Ile Cys Tyr Asn His Leu Gly Thr Lys Pro Pro Thr Thr Glu Thr
  1               5                  10                  15
```

-continued

```
Cys Gln Glu Asp Ser Cys Tyr Lys Asn Ile Trp Thr Phe Asp Asn Ile
            20                  25                  30

Ile Arg Arg Gly Cys Gly Cys Phe Thr Pro Arg Gly Asp Met Pro Gly
        35                  40                  45

Ala Tyr Cys Cys Glu Ser Asp Lys Cys Asn Leu
    50                  55


<210> SEQ ID NO 31
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 31

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
            20                  25                  30

Ile Arg Arg Gly Cys Gly Cys Phe Ala Pro Arg Gly Asp Met Pro Gly
        35                  40                  45

Pro Tyr Cys Cys Glu Ser Asp Lys Cys Asn Leu
    50                  55


<210> SEQ ID NO 32
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 32

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
            20                  25                  30

Ile Arg Arg Gly Cys Gly Cys Phe Thr Pro Arg Gly Asp Phe Pro Gly
        35                  40                  45

Pro Tyr Cys Cys Glu Ser Asp Lys Cys Asn Leu
    50                  55


<210> SEQ ID NO 33
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 33

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
            20                  25                  30

Ile Arg Arg Gly Cys Gly Cys Phe Thr Pro Arg Gly Asp Trp Pro Gly
        35                  40                  45

Pro Tyr Cys Cys Glu Ser Asp Lys Cys Asn Leu
    50                  55
```

-continued

```
<210> SEQ ID NO 34
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 34

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Ser Pro Gly
         35                  40                  45

Pro Tyr Cys Cys Glu Ser Asp Lys Cys Asn Leu
     50                  55


<210> SEQ ID NO 35
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 35

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Asp Pro Gly
         35                  40                  45

Pro Tyr Cys Cys Glu Ser Asp Lys Cys Asn Leu
     50                  55


<210> SEQ ID NO 36
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 36

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp His Pro Gly
         35                  40                  45

Pro Tyr Cys Cys Glu Ser Asp Lys Cys Asn Leu
     50                  55


<210> SEQ ID NO 37
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 37
```

-continued

```
Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Met Pro Gly
         35                  40                  45

Pro Arg Cys Cys Glu Ser Asp Lys Cys Asn Leu
     50                  55


<210> SEQ ID NO 38
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 38

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Met Pro Gly
         35                  40                  45

Pro Thr Cys Cys Glu Ser Asp Lys Cys Asn Leu
     50                  55


<210> SEQ ID NO 39
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 39

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Met Leu Asp
         35                  40                  45

Pro Tyr Cys Cys Glu Ser Asp Lys Cys Asn Leu
     50                  55


<210> SEQ ID NO 40
<211> LENGTH: 59
<212> TYPE: PRT
<213> ORGANISM: Artificial Sequence
<220> FEATURE:
<223> OTHER INFORMATION: Description of Artificial Sequence: modified
      dendroaspin

<400> SEQUENCE: 40

Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Arg Gly Asp Met Pro Asp
         35                  40                  45

Asp Tyr Cys Cys Glu Ser Asp Lys Cys Asn Leu
```

-continued 50 55

<210> SEQ ID NO 41
<211> LENGTH: 59
<212> TYPE: PRT
<213> ORGANISM: Artificial Sequence
<220> FEATURE:
<223> OTHER INFORMATION: Description of Artificial Sequence: modified dendroaspin

<400> SEQUENCE: 41

```
Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Lys Gly Asp Met Pro Gly
         35                  40                  45

Pro Tyr Cys Cys Glu Ser Asp Lys Cys Asn Leu
     50                  55
```

<210> SEQ ID NO 42
<211> LENGTH: 59
<212> TYPE: PRT
<213> ORGANISM: Artificial Sequence
<220> FEATURE:
<223> OTHER INFORMATION: Description of Artificial Sequence: modified dendroaspin

<400> SEQUENCE: 42

```
Arg Ile Cys Tyr Asn His Leu Gly Thr Lys Pro Pro Thr Thr Glu Thr
  1               5                  10                  15

Cys Gln Glu Asp Ser Cys Tyr Lys Asn Ile Trp Thr Phe Asp Asn Ile
             20                  25                  30

Ile Arg Arg Gly Cys Gly Cys Phe Thr Pro Lys Gly Asp Trp Pro Gly
         35                  40                  45

Pro Tyr Cys Cys Glu Ser Asp Lys Cys Asn Leu
     50                  55
```

<210> SEQ ID NO 43
<211> LENGTH: 72
<212> TYPE: PRT
<213> ORGANISM: Artificial Sequence
<220> FEATURE:
<223> OTHER INFORMATION: Description of Artificial Sequence: modified dendroaspin

<400> SEQUENCE: 43

```
Arg Ile Cys Phe Thr Pro Arg Gly Asp Met Pro Gly Pro Tyr Pro Gly
  1               5                  10                  15

Pro Cys Gln Glu Asp Ser Cys Tyr Lys Asn Ile Trp Thr Phe Asp Asn
             20                  25                  30

Ile Ile Arg Arg Gly Cys Gly Cys Phe Thr Pro Arg Gly Asp Met Pro
         35                  40                  45

Gly Pro Tyr Phe Pro Arg Pro Gln Ser His Asn Asp Gly Asp Phe Glu
     50                  55                  60

Glu Ile Pro Glu Glu Tyr Leu Gln
 65                  70
```

<210> SEQ ID NO 44
<211> LENGTH: 70
<212> TYPE: PRT
<213> ORGANISM: Artificial Sequence -continued
<220> FEATURE:
<223> OTHER INFORMATION: Description of Artificial Sequence: modified
dendroaspin

<400> SEQUENCE: 44

Arg Ile Cys Phe Thr Pro Arg Gly Asp Met Pro Gly Pro Tyr Pro Gly
1 5 10 15

Pro Cys Gln Glu Asp Ser Cys Tyr Lys Asn Ile Trp Thr Phe Asp Asn
20 25 30

Ile Ile Arg Arg Gly Cys Gly Cys Phe Thr Pro Arg Gly Asp Met Pro
35 40 45

Gly Pro Tyr Glu Cys Pro Glu Gly Tyr Ile Leu Asp Asp Gly Phe Ile
50 55 60

Cys Thr Asp Ile Asp Glu
65 70

<210> SEQ ID NO 45
<211> LENGTH: 66
<212> TYPE: PRT
<213> ORGANISM: Artificial Sequence
<220> FEATURE:
<223> OTHER INFORMATION: Description of Artificial Sequence: modified
dendroaspin

<400> SEQUENCE: 45

Arg Ile Cys Phe Thr Pro Arg Gly Asp Met Pro Gly Pro Tyr Pro Gly
1 5 10 15

Pro Cys Gln Glu Asp Ser Cys Tyr Lys Asn Ile Trp Thr Phe Asp Asn
20 25 30

Ile Ile Arg Arg Gly Cys Gly Cys Phe Thr Pro Arg Gly Asp Met Pro
35 40 45

Gly Pro Tyr Gly Asp Thr Asp Leu Tyr Asp Tyr Tyr Pro Glu Glu Asp
50 55 60

Thr Glu
65

<210> SEQ ID NO 46
<211> LENGTH: 52
<212> TYPE: PRT
<213> ORGANISM: Artificial Sequence
<220> FEATURE:
<223> OTHER INFORMATION: Description of Artificial Sequence: modified
dendroaspin

<400> SEQUENCE: 46

Arg Ile Cys Phe Thr Pro Arg Gly Asp Met Pro Gly Pro Tyr Pro Gly
1 5 10 15

Pro Cys Gln Glu Asp Ser Cys Tyr Lys Asn Ile Trp Thr Phe Asp Asn
20 25 30

Ile Ile Arg Arg Gly Pro Gly Pro Thr Trp Thr Ala Asn Val Gly Lys
35 40 45

Gly Gln Pro Ser
50

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: bases
921-956 of pGEX-3X -continued

<400> SEQUENCE: 47
atcgaaggtc gtgggatccc cgggaattca tcgtgactga ctgac 45

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: amino acids encoded by bases 921-956 of pGEX-3X

<400> SEQUENCE: 48

Ile Glu Gly Arg Gly Ile Pro Gly Asn Ser Ser
1 5 10